(12) United States Patent
Davagian et al.

(10) Patent No.: US 12,337,130 B2
(45) Date of Patent: Jun. 24, 2025

(54) SUPPOSITORY INSERTION DEVICE, SUPPOSITORY, AND METHOD OF MANUFACTURING A SUPPOSITORY

(71) Applicant: Cristcot LLC, Concord, MA (US)

(72) Inventors: Jennifer J. Davagian, Acton, MA (US); Mark C. Ensign, Sudbury, MA (US)

(73) Assignee: Cristcot LLC, Concord, MA (US)

( * ) Notice: Subject to any disclaimer, the term of this patent is extended or adjusted under 35 U.S.C. 154(b) by 809 days.

(21) Appl. No.: 17/533,308

(22) Filed: Nov. 23, 2021

(65) Prior Publication Data
US 2022/0088358 A1 Mar. 24, 2022

Related U.S. Application Data

(62) Division of application No. 16/197,005, filed on Nov. 20, 2018, now Pat. No. 11,224,727, which is a
(Continued)

(51) Int. Cl.
*A61M 31/00* (2006.01)
*A45D 40/16* (2006.01)
(Continued)

(52) U.S. Cl.
CPC .......... *A61M 31/007* (2013.01); *A45D 40/16* (2013.01); *A61B 50/30* (2016.02); *A61J 3/08* (2013.01);
(Continued)

(58) Field of Classification Search
CPC ......... A61B 50/30; A61J 3/08; A61M 31/007; A45D 40/16; A45D 40/00; A45D 40/08;
(Continued)

(56) References Cited

U.S. PATENT DOCUMENTS 330,764 A 11/1885 Worley
504,512 A 9/1893 Bailey
(Continued)

FOREIGN PATENT DOCUMENTS

CN 2416896 Y 1/2001
CN 201586319 U 9/2010
(Continued)

OTHER PUBLICATIONS

Amendment under Article 34 and Reply to Written Opinion filed in International Application No. PCT/US2009/059623 "Method and Apparatus for Inserting a Rectal Suppository," mailed on Sep. 16, 2010.
(Continued)

*Primary Examiner* — Monica A Huson
(74) *Attorney, Agent, or Firm* — Foley & Lardner LLP

(57) ABSTRACT

Today's suppositories are typically packaged individually for digital administration into the anal canal of a patient. A suppository applicator described herein, which works with individually packaged suppositories, can alternatively be shipped in a prepackaged operational arrangement with a suppository to enable the patient to administer the suppository through use of the applicator in a single operation after opening a hygienic wrapper containing the applicator-suppository combination. A method for manufacturing a suppository includes manufacturing the suppository in the presence of and in contact with an element configured to be used to insert the suppository into a body cavity. The method may include using the element to define a shape of the suppository during the manufacturing. The resulting applicator-suppository combination is more hygienic and easier to handle than the separate applicator and suppository and provides more efficiency from time of opening the packag-
(Continued)

ing to time of commencing administration of the suppository.

13 Claims, 34 Drawing Sheets

Related U.S. Application Data division of application No. 14/436,359, filed as application No. PCT/US2013/065795 on Oct. 18, 2013, now Pat. No. 10,149,967.

(60) Provisional application No. 61/807,915, filed on Apr. 3, 2013, provisional application No. 61/716,212, filed on Oct. 19, 2012.

(51) Int. Cl.
| | |
|---|---|
| *A61B 50/30* | (2016.01) |
| *A61J 3/08* | (2006.01) |
| *A45D 40/00* | (2006.01) |
| *A45D 40/08* | (2006.01) |
| *A45D 40/12* | (2006.01) |
| *A45D 40/20* | (2006.01) |
| *A61K 9/00* | (2006.01) |
| *A61K 9/02* | (2006.01) |

(52) U.S. Cl.
CPC ............. *A45D 40/00* (2013.01); *A45D 40/08* (2013.01); *A45D 40/12* (2013.01); *A45D 2040/202* (2013.01); *A61K 9/0031* (2013.01); *A61K 9/025* (2013.01)

(58) Field of Classification Search
CPC .. A45D 2040/202; A45D 40/12; A61K 9/025; A61K 9/0031
See application file for complete search history.

(56) References Cited

U.S. PATENT DOCUMENTS

| | | | |
|---|---|---|---|
| 2,281,600 A | 5/1942 | Ross | |
| 2,290,571 A | 7/1942 | Peyton | |
| 2,443,207 A | 6/1948 | Tedford | |
| 2,503,445 A | 4/1950 | Lermer | |
| 2,532,598 A | 12/1950 | Boeger | |
| 2,680,442 A | 6/1954 | Linzmayer | |
| 2,709,436 A | 5/1955 | Lynn | |
| 2,754,823 A | 7/1956 | Miller | |
| 3,015,332 A | 1/1962 | Brecht | |
| 3,139,886 A | 7/1964 | Tallman et al. | |
| 3,220,413 A | 11/1965 | Sunnen | |
| 3,667,465 A | 6/1972 | Voss | |
| 3,780,735 A | 12/1973 | Crouter et al. | |
| 3,835,856 A | 9/1974 | Warncke | |
| 3,840,010 A | 10/1974 | Giglio | |
| 4,248,229 A | 2/1981 | Miller | |
| 4,341,211 A | 7/1982 | Kline | |
| 4,341,221 A | 7/1982 | Testerman | |
| 4,361,150 A | 11/1982 | Voss | |
| 4,406,655 A | 9/1983 | Clayton | |
| 4,421,504 A | 12/1983 | Kline | |
| 4,752,288 A | 6/1988 | Hussey | |
| 4,990,136 A | 2/1991 | Geria | |
| 5,152,068 A | 10/1992 | Meister et al. | |
| D330,764 S | 11/1992 | Lorentzon | |
| 5,160,689 A | 11/1992 | Kamen | |
| 5,213,566 A | 5/1993 | Weissenburger | |
| 5,330,427 A | 7/1994 | Weissenburger | |
| 5,352,681 A | 10/1994 | Wittebrood et al. | |
| 5,354,325 A | 10/1994 | Chive et al. | |
| 5,360,281 A * | 11/1994 | Kamen ................. | A45D 40/16 264/46.1 |
| 5,460,617 A | 10/1995 | Minkus et al. | |
| 5,656,283 A | 8/1997 | Brummer et al. | |
| 5,662,601 A | 9/1997 | Snead | |
| 5,788,664 A | 8/1998 | Scalise | |
| 5,860,946 A | 1/1999 | Hofstätter | |
| 6,056,714 A | 5/2000 | McNelis et al. | |
| D436,661 S | 1/2001 | Berry | |
| 6,190,348 B1 | 2/2001 | Tiemann et al. | |
| 6,245,776 B1 | 6/2001 | Skwierczynski et al. | |
| 6,380,455 B1 | 4/2002 | Moder et al. | |
| 6,486,168 B1 | 11/2002 | Skwierczynski et al. | |
| 6,500,460 B1 | 12/2002 | Bergeron et al. | |
| D471,980 S | 3/2003 | Caizza | |
| 6,706,728 B2 | 3/2004 | Hedenstrom et al. | |
| 6,740,333 B2 | 5/2004 | Beckett et al. | |
| 6,786,883 B2 | 9/2004 | Shippert | |
| 6,916,308 B2 | 7/2005 | Dixon et al. | |
| 7,070,581 B2 | 7/2006 | Manera et al. | |
| 7,081,110 B2 | 7/2006 | Karapasha | |
| 7,104,968 B2 | 9/2006 | Swick | |
| D529,603 S | 10/2006 | Knickerbocker et al. | |
| 7,122,025 B1 | 10/2006 | Nestenborg | |
| 7,149,574 B2 | 12/2006 | Yun et al. | |
| 7,192,607 B2 | 3/2007 | Bergeron et al. | |
| 7,198,612 B2 | 4/2007 | Swick | |
| 7,217,252 B2 | 5/2007 | Swick | |
| 7,361,168 B2 | 4/2008 | Makower et al. | |
| D572,362 S | 7/2008 | Edgett et al. | |
| D579,786 S | 11/2008 | Py et al. | |
| 7,465,295 B2 | 12/2008 | Bergeron et al. | |
| D585,988 S | 2/2009 | Kinnard | |
| 7,503,895 B2 | 3/2009 | Rabiner et al. | |
| 7,591,808 B2 | 9/2009 | DiPiano et al. | |
| D608,659 S | 1/2010 | Py et al. | |
| 7,666,160 B2 | 2/2010 | Rajala et al. | |
| 8,192,393 B2 | 6/2012 | Ensign | |
| 8,419,712 B2 | 4/2013 | Ensign | |
| 9,662,481 B2 | 5/2017 | Davagian | |
| 10,149,967 B2 | 12/2018 | Davagian et al. | |
| 10,525,242 B2 | 1/2020 | Davagian | |
| 11,224,727 B2 * | 1/2022 | Davagian ................. | A61J 3/08 |
| 11,298,515 B2 | 4/2022 | Davagian | |
| 2002/0048601 A1 | 4/2002 | Beckett et al. | |
| 2002/0058674 A1 | 5/2002 | Hedenstrom et al. | |
| 2003/0045543 A1 | 3/2003 | Hedenstrom et al. | |
| 2003/0088217 A1 | 5/2003 | Bergeron et al. | |
| 2003/0233077 A1 | 12/2003 | Swick | |
| 2003/0233078 A1 | 12/2003 | Swick | |
| 2004/0047910 A1 | 3/2004 | Beckett et al. | |
| 2004/0249352 A1 | 12/2004 | Swick | |
| 2004/0249416 A1 | 12/2004 | Yun et al. | |
| 2004/0260252 A1 | 12/2004 | DiPiano et al. | |
| 2005/0004533 A1 | 1/2005 | Smith | |
| 2005/0021092 A1 | 1/2005 | Yun et al. | |
| 2005/0143378 A1 | 6/2005 | Yun et al. | |
| 2005/0143788 A1 | 6/2005 | Yun et al. | |
| 2005/0153885 A1 | 7/2005 | Yun et al. | |
| 2005/0240241 A1 | 10/2005 | Yun et al. | |
| 2005/0256028 A1 | 11/2005 | Yun et al. | |
| 2005/0273038 A1 | 12/2005 | Osborn, III et al. | |
| 2006/0034847 A1 | 2/2006 | Yun et al. | |
| 2006/0035974 A1 | 2/2006 | Yun et al. | |
| 2006/0069012 A1 | 3/2006 | Yun et al. | |
| 2006/0161105 A1 | 7/2006 | Mori et al. | |
| 2006/0184100 A1 | 8/2006 | Studin | |
| 2006/0206149 A1 | 9/2006 | Yun | |
| 2007/0073267 A1 | 3/2007 | Muller | |
| 2007/0112327 A1 | 5/2007 | Yun et al. | |
| 2007/0129668 A1 | 6/2007 | Swick | |
| 2007/0185436 A1 | 8/2007 | Swick | |
| 2008/0038377 A1 | 2/2008 | Citow | |
| 2008/0097286 A1 | 4/2008 | Cleator et al. | |
| 2008/0161752 A1 | 7/2008 | Rajala et al. | |
| 2008/0167598 A1 | 7/2008 | Gann et al. | |
| 2008/0167599 A1 | 7/2008 | Osborn et al. | |
| 2008/0300575 A1 | 12/2008 | Cleator et al. | |
| 2008/0319269 A1 | 12/2008 | Longo et al. | |
| 2010/0010471 A1 | 1/2010 | Ladd et al. | |
| 2010/0087797 A1 | 4/2010 | Ensign | |

(56) References Cited

U.S. PATENT DOCUMENTS

| | | |
|---|---|---|
| 2010/0145379 A1 | 6/2010 | Isham |
| 2013/0204182 A1 | 8/2013 | Ensign |
| 2015/0265820 A1 | 9/2015 | Ensign et al. |
| 2017/0224971 A1 | 8/2017 | Davagian |
| 2019/0143088 A1 | 5/2019 | Davagian |
| 2019/0151636 A1 | 5/2019 | Davagian et al. |
| 2022/0288367 A1 | 9/2022 | Davagian |

FOREIGN PATENT DOCUMENTS

| | | |
|---|---|---|
| DE | 3031408 A1 | 3/1982 |
| EP | 1 040 808 A2 | 10/2000 |
| EP | 1 319 420 A1 | 6/2003 |
| EP | 1 530 978 A1 | 5/2005 |
| EP | 2554211 A1 | 2/2013 |
| FR | 1 190 750 A | 10/1959 |
| FR | 2923999 A1 | 5/2009 |
| JP | S59-181834 U | 12/1984 |
| JP | H02-302266 A | 12/1990 |
| JP | H05-070545 U | 9/1993 |
| JP | H05-279243 A | 10/1993 |
| JP | H09-103467 A | 4/1997 |
| JP | 2001-070456 A | 3/2001 |
| JP | 2004-526520 A | 9/2004 |
| JP | 2007-215732 A | 8/2007 |
| JP | 20125719 A | 1/2012 |
| WO | WO 01/91605 | 12/2001 |
| WO | WO 03/101525 A1 | 12/2003 |
| WO | WO 2004/112755 A1 | 12/2004 |
| WO | WO 2006/063377 A1 | 6/2006 |
| WO | WO 2006/077617 A1 | 7/2006 |
| WO | WO 2008/018353 A1 | 7/2008 |
| WO | WO 2008/084453 A1 | 7/2008 |
| WO | WO 2008/102341 A2 | 8/2008 |
| WO | WO 2010/042468 A2 | 4/2010 |
| WO | WO 2014/063122 A1 | 4/2014 |
| WO | WO 2017/197100 | 11/2017 |

OTHER PUBLICATIONS

Banerjee, S., et al., "Inflammatory Bowel Disease Medical Therapy of Specific Clinical Presentations," *Gastroenterol Clin N Am*, 31: 185-202 (2002).

Bradshaw, A., "Rectal Suppository Insertion: The Reliability of the Evidence as a Basis for Nursing Practice," *Journal of Clinical Nursing*, 16: 98-103 (2006).

Expedited Review Request, Letter and Attachments A/C from Jennifer Davagian Ensign regarding Expedited Review of 510(k) Premarket Notification, dated Sep. 4, 2009.

Fernandez/Becker, N. Q., et al., "Improving Delivery of Aminosalicylates in Ulcerative Colitis," *Drugs*, 68(8): 1089-1103 (2008).

Hidaka, N., et al., "Changes in the Plasma Diazepam Concentration and Its Anticonvulsant Effect After the Discharge of a Diazepam Suppository from the Rectum in Rats," *Methods Find Exp Clin Pharmacol*, 29(6): 401-404 (2007).

Howell, H. R., "Ulcerative Colitis: Achieving and Maintaining Remission," *US Pharm*, 33(12): 30-37 (2008).

International Preliminary Report on Patentability and Written Opinion of the International Searching Authority, PCT/US2013/065795, "Suppository Insertion Device, Suppository, And Method Of Manufacturing A Suppository", Date of Issuance Apr. 21, 2015.

International Preliminary Report on Patentability from International Application No. PCT/US2009/059623 "Method and Apparatus for Inserting a Rectal Suppository," mailed on Mar. 28, 2011.

International Search Report and Written Opinion for Int'l Application No. PCT/US2013/065795, titled: Suppository Insertion Device, Suppository, And Method Of Manufacturing A Suppository, Date of Mailing: Feb. 7, 2014.

International Search Report and Written Opinion for PCT/US2017/032142, dated Aug. 29, 2017, entitled "Single/Use Suppository Insertion Device And Method," 14 pages.

International Search Report and Written Opinion of the International Searching Authority from International Application No. PCT/US2009/059623 "Method and Apparatus for Inserting a Rectal Suppository," mailed on Jun. 16, 2010.

Partial European Search Report for Application No. 17168072.1/1653, dated Oct. 4, 2017, entitled "Suppository Insertion Device, Suppository, And Method Of Manufacturing A Suppository," 12 pages.

Regueiro, M., et al., "Medical Management of Left/Sided Ulcerative Colitis and Ulcerative Proctitis: Critical Evaluation of Therapeutic Trials," *Inflamm Bowel Dis*, 12(10): 979-994 (2006).

Tindall, W. N., et al., "Mild/to/Moderate Ulcerative Colitis: Your Role in Patient Compliance and Health Care Costs," *Supplement to Journal of Managed Care Pharmacy*, 13(7, S/a): S2-S15 (2007) (with attached 2/page Evaluation).

Non-final Office Action for U.S. Appl. No. 16/197,005, Date Mailed: Apr. 1, 2021.

Notice of Allowance for U.S. Appl. No. 16/197,005, Date Mailed: Sep. 22, 2021.

\* cited by examiner

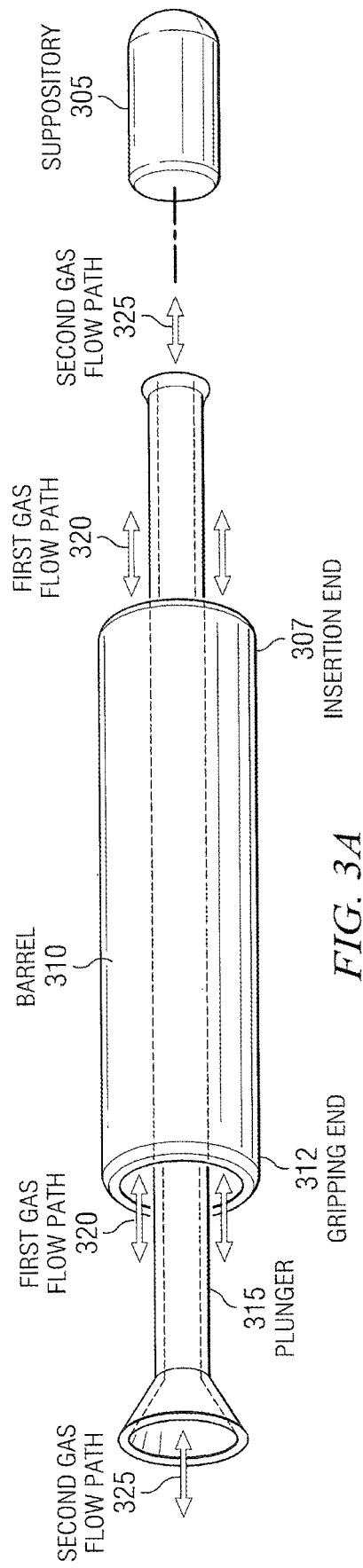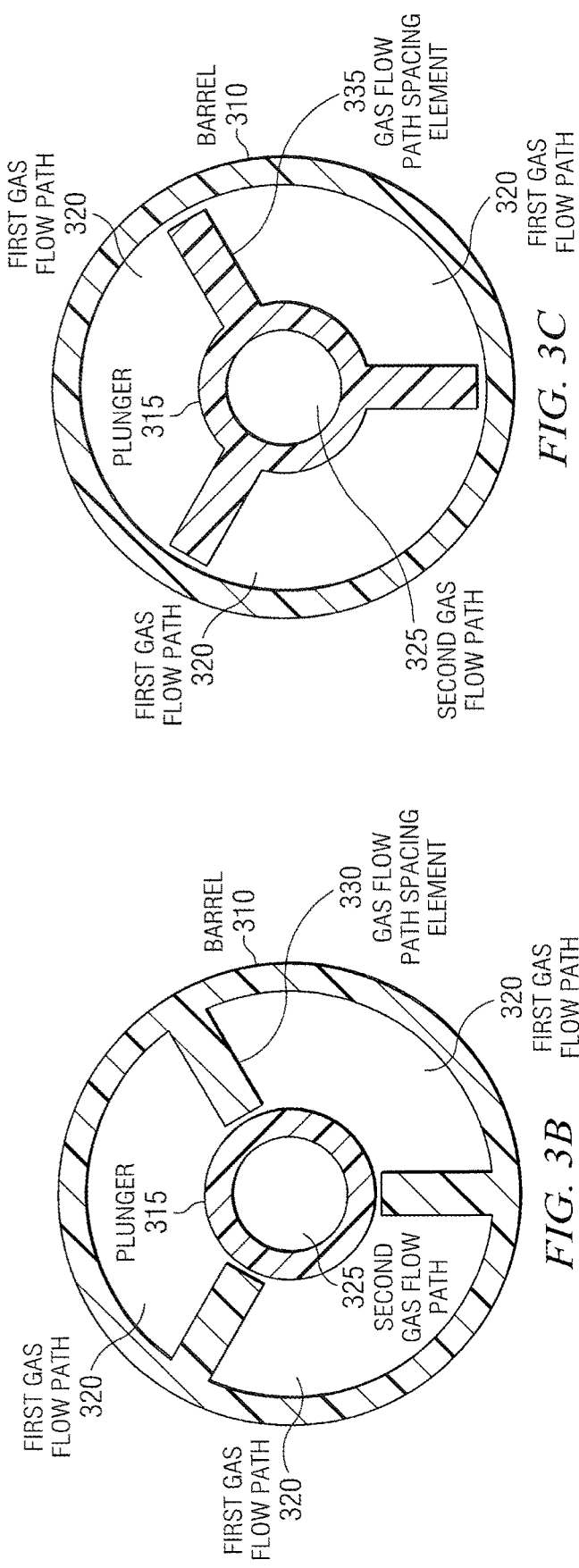

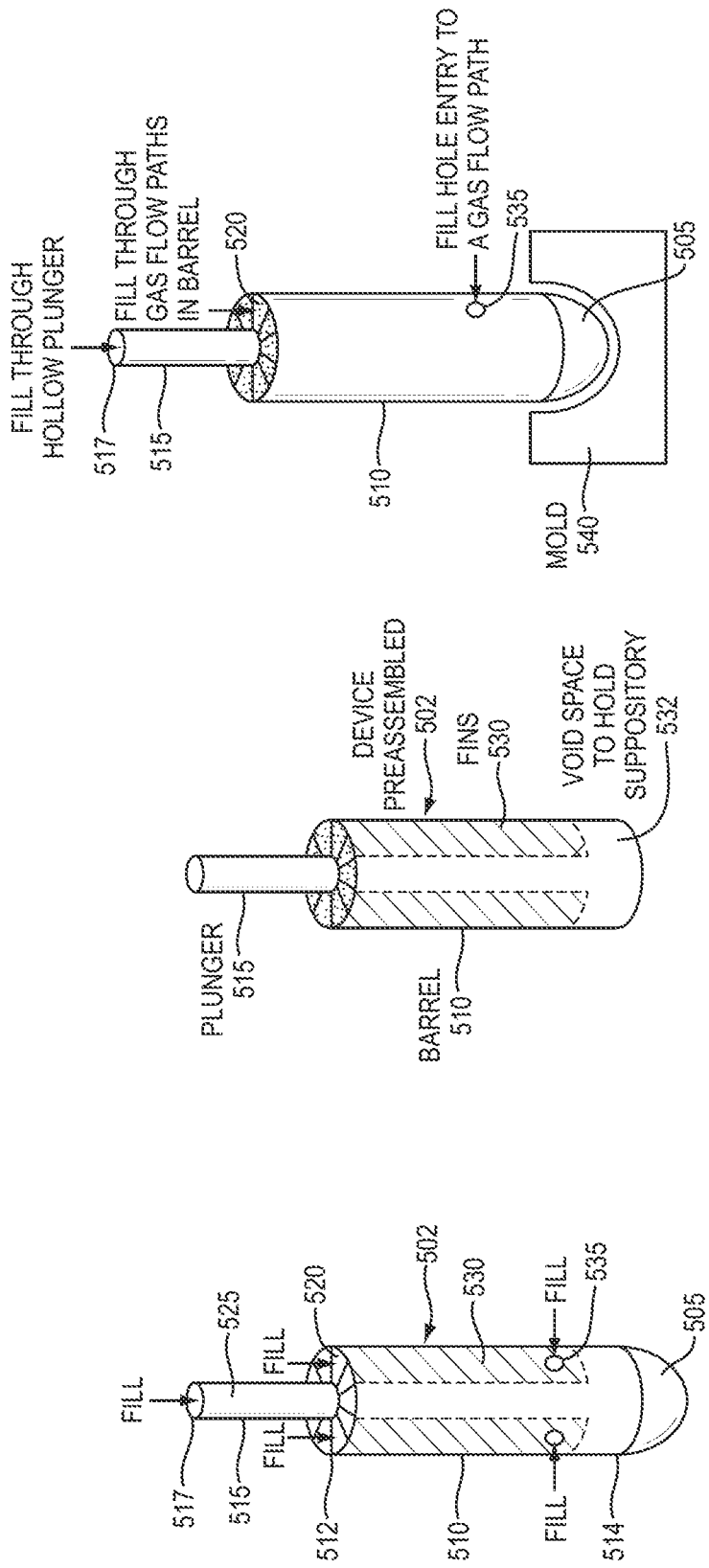

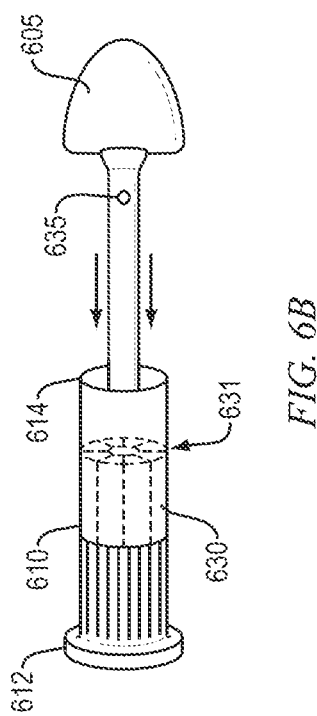
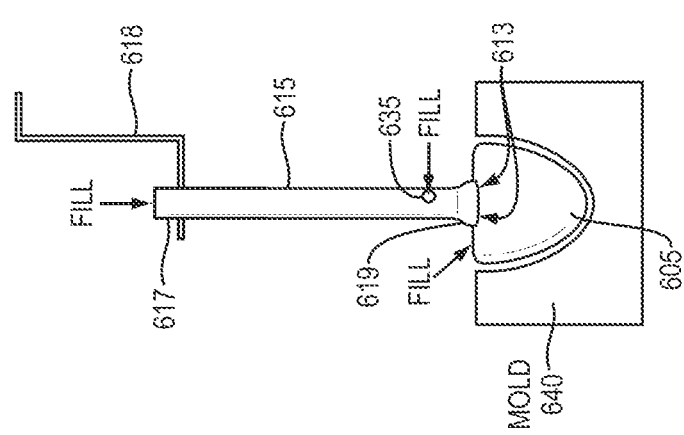
FIG. 6B
FIG. 6A

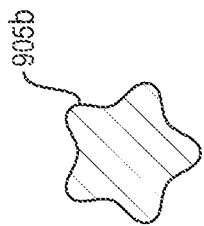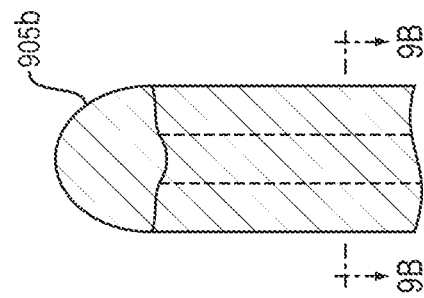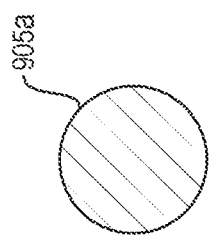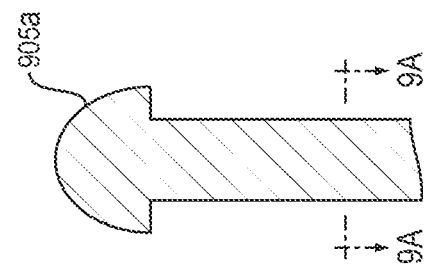

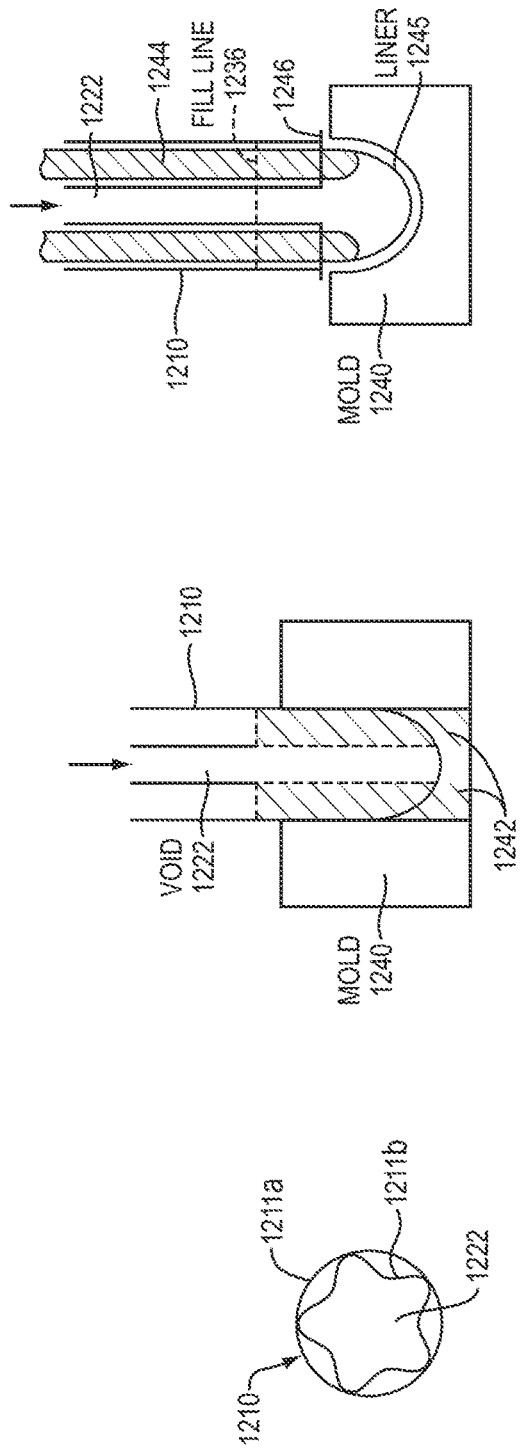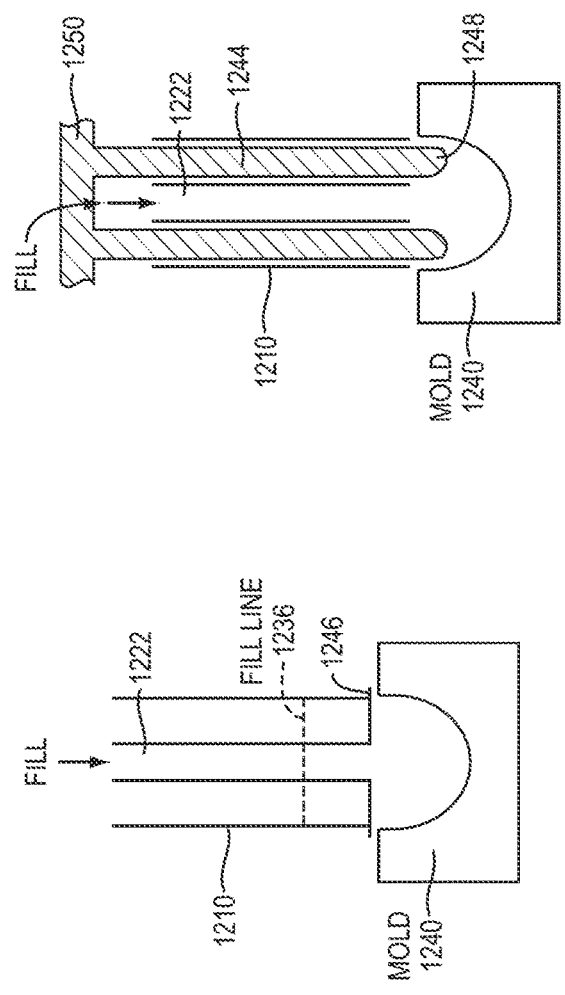

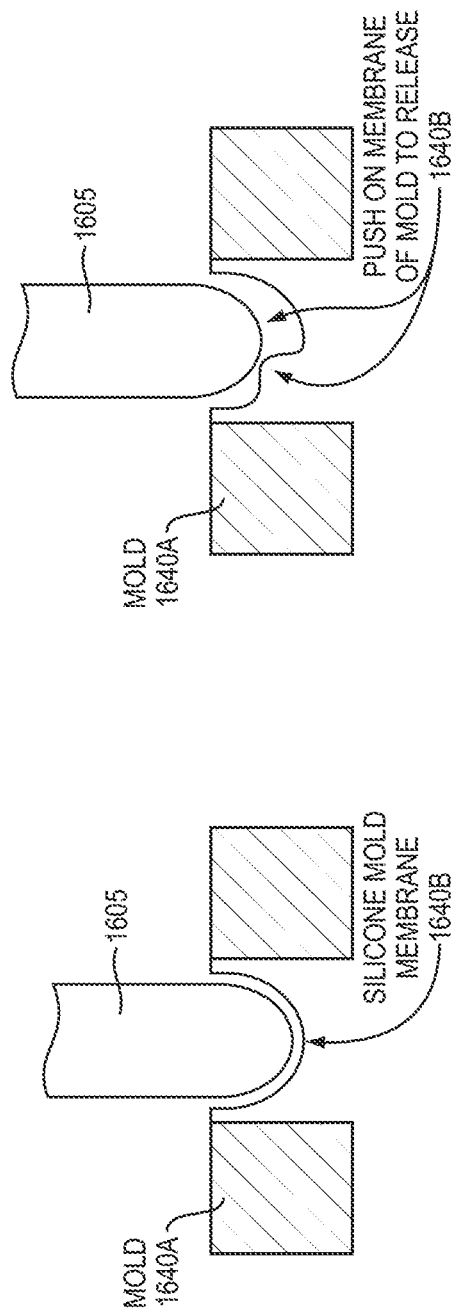
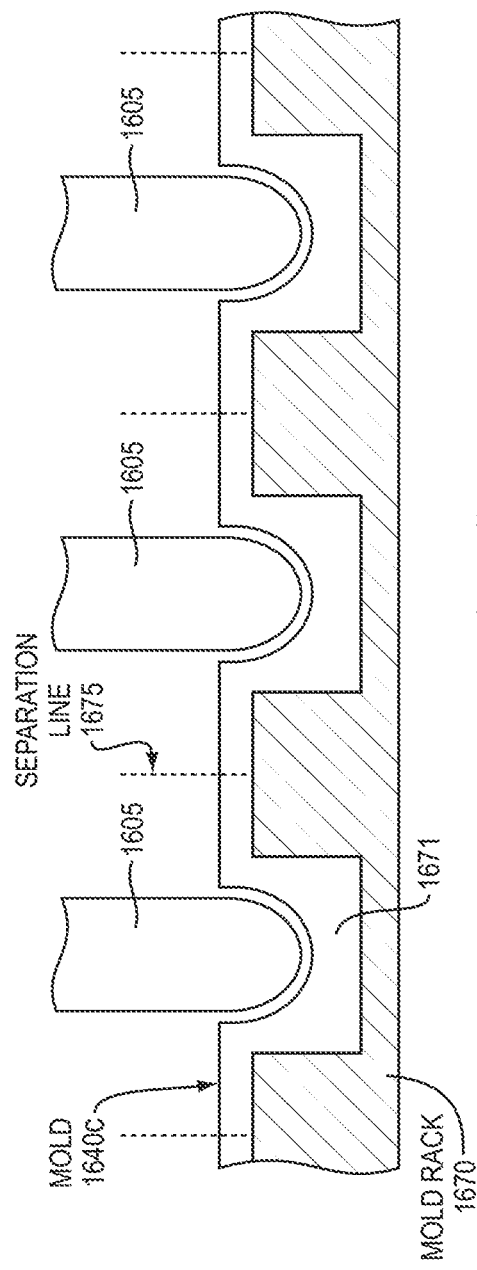

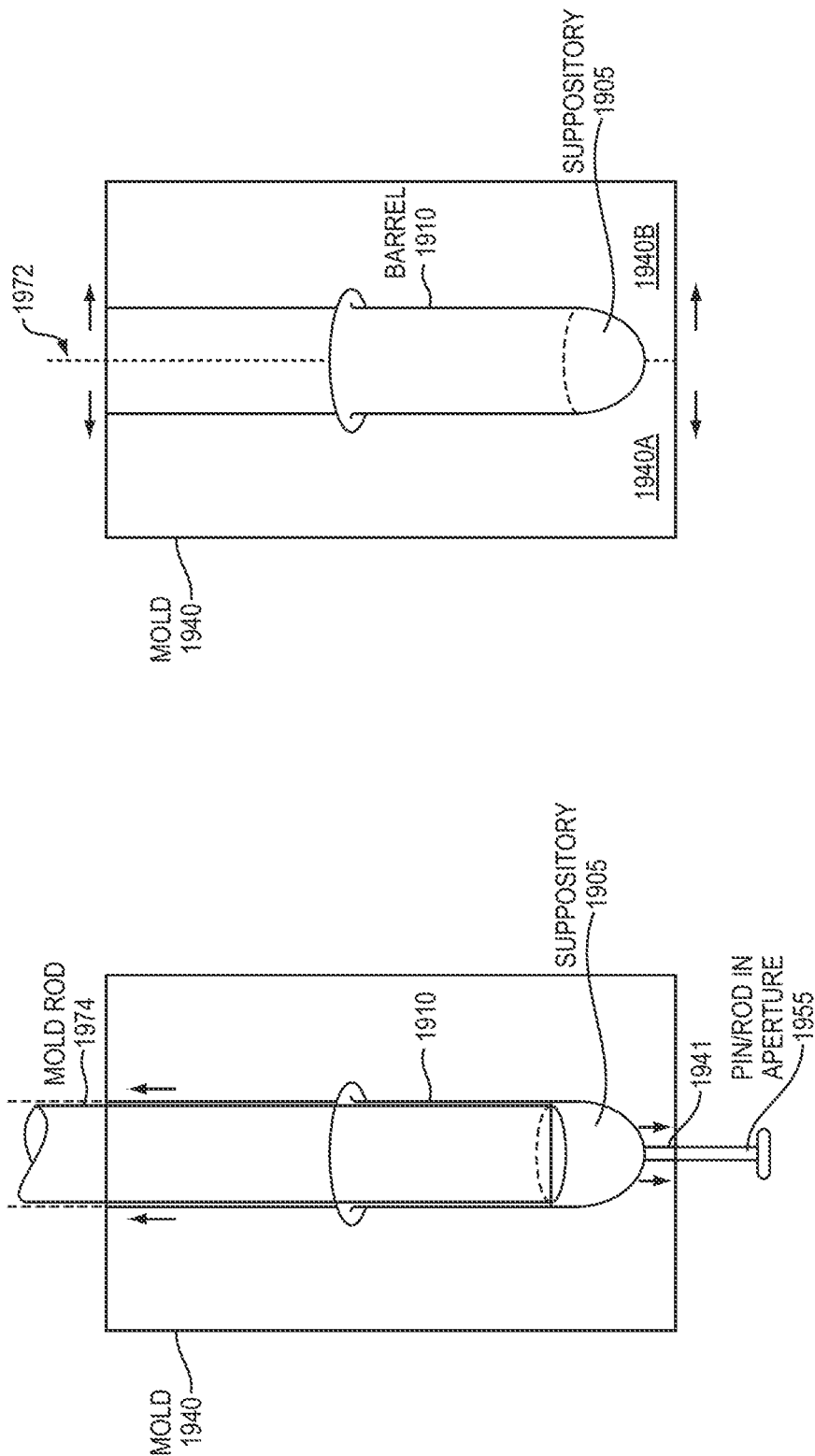

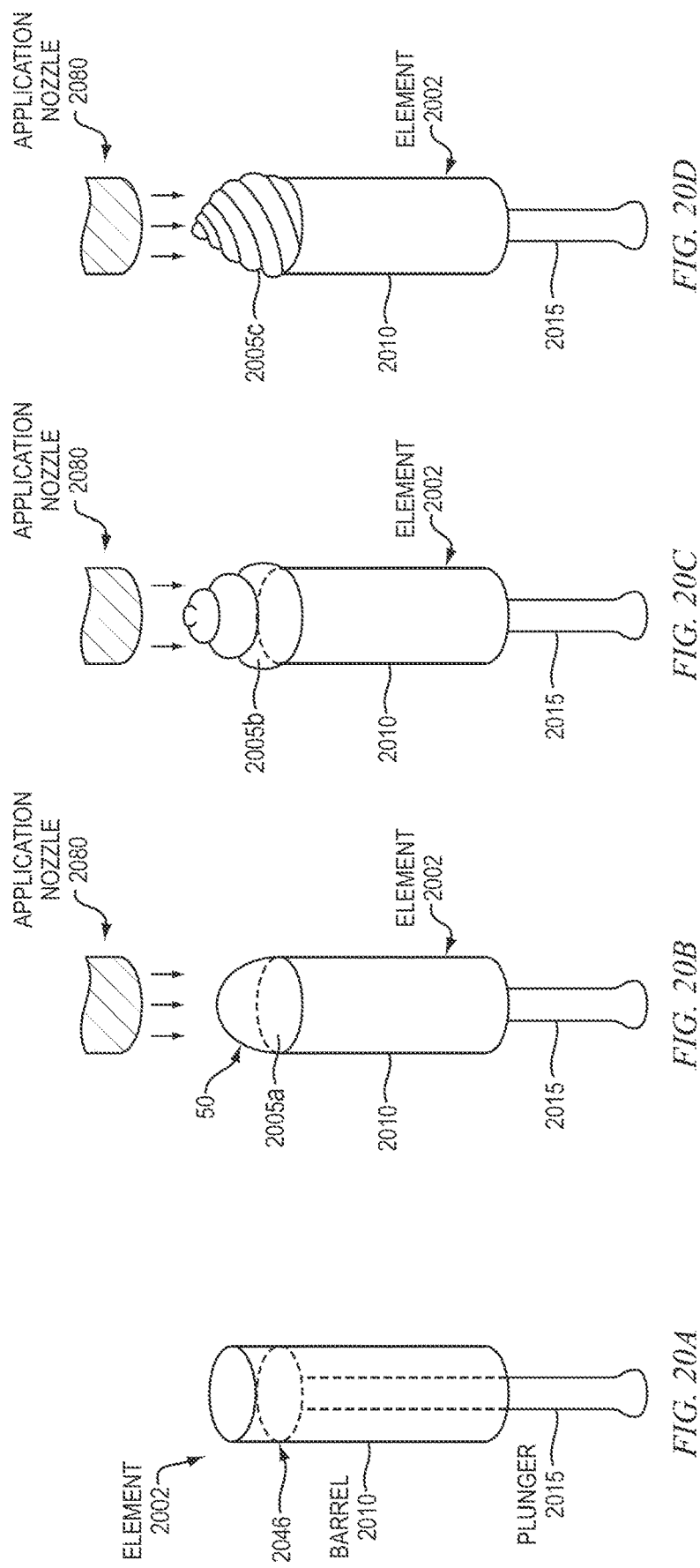

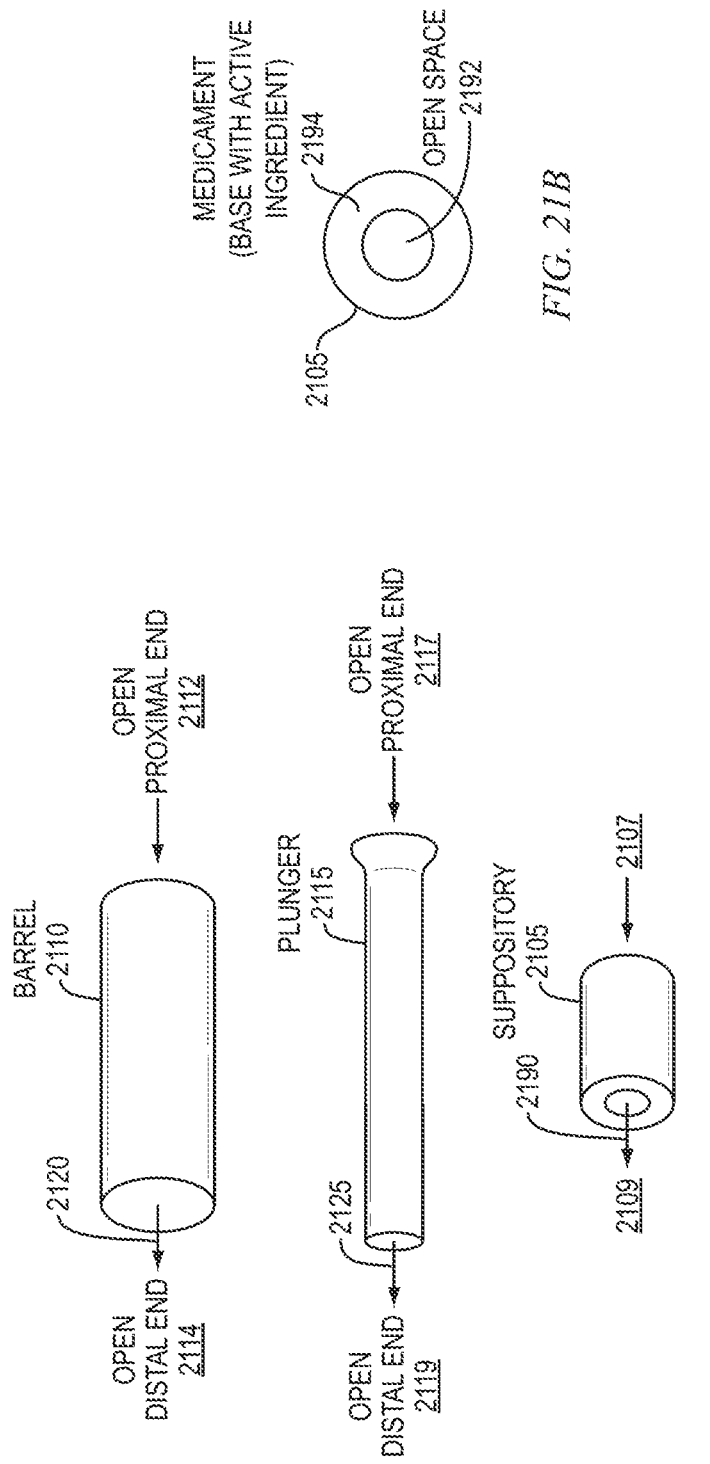

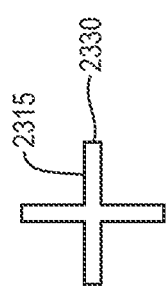
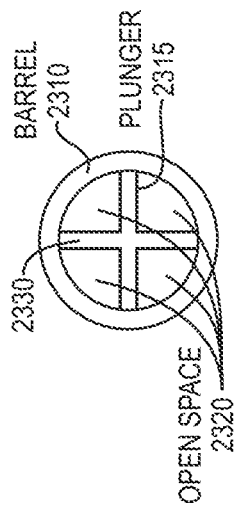
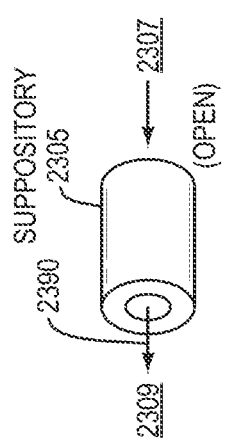
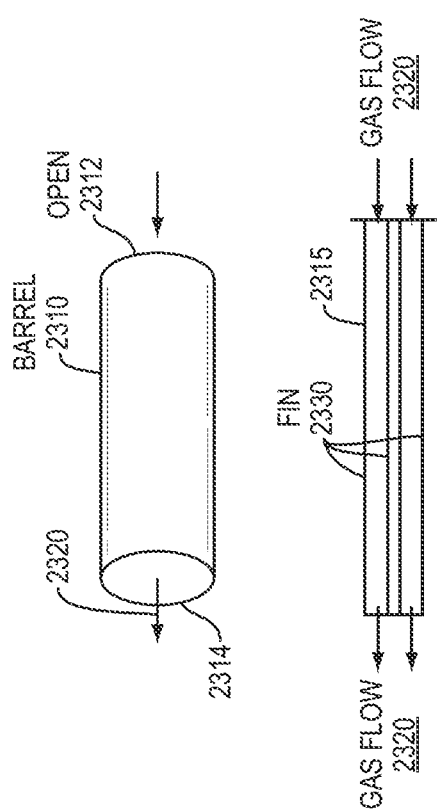
FIG. 23B
FIG. 23C
FIG. 23D
FIG. 23A

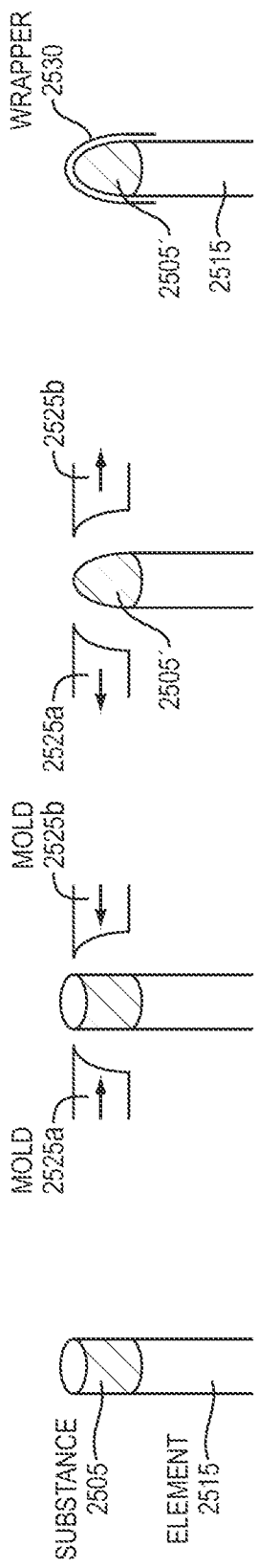
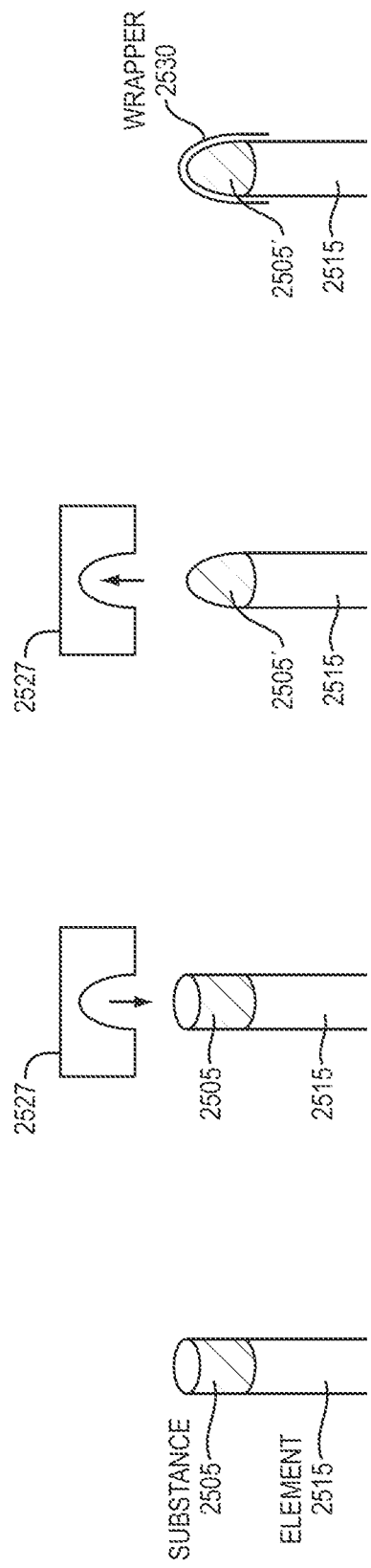

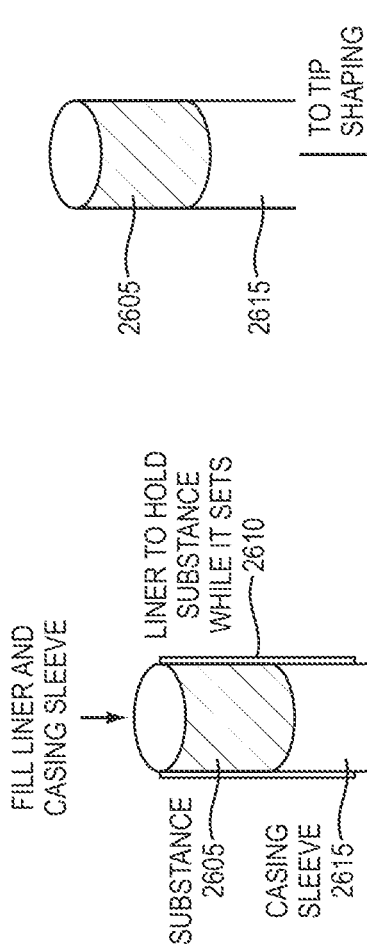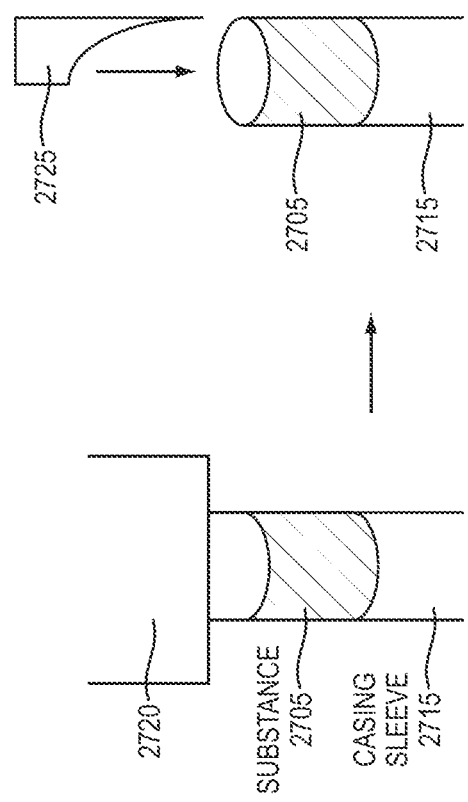

EXAMPLES OF CATEGORIES OF
TIP SHAPES OF LIPSTICKS

SUPPOSITORY INSERTION DEVICE, SUPPOSITORY, AND METHOD OF MANUFACTURING A SUPPOSITORY

RELATED APPLICATIONS

This application is a divisional of U.S. application Ser. No. 16/197,005, filed on Nov. 20, 2018, which is a divisional of U.S. application Ser. No. 14/436,359, filed on Apr. 16, 2015, now U.S. Pat. No. 10,149,967, which is the U.S. National Stage of International Application No. PCT/US2013/065795, filed on Oct. 18, 2013, published in English, which claims the benefit of U.S. Provisional Application No. 61/716,212, filed on Oct. 19, 2012 and U.S. Provisional Application No. 61/807,915, filed on Apr. 3, 2013. The entire teachings of the above applications are incorporated herein by reference.

BACKGROUND OF THE INVENTION

Suppositories are typically packaged individually or as a group within a package. Applicators are typically packaged separately, and suppositories and applicators are often sold together within the same box. When the patient is ready to use the product, the patient first opens the box, unwraps a suppository, opens one applicator device, and then arranges the suppository within the device. After arranging the suppository within the applicator, the patient can administer the medication according to the instructions for use.

Rectal medications are used to treat symptoms in a variety of patient populations. Certain medical conditions, such as gastrointestinal diseases, may be more effectively treated when the medication is placed in a particular location of the patient's anal canal or rectum. Medication delivered rectally is absorbed by the mucosa lining of the rectum treating a patient locally or systemically. Rectally administered medication enters the bloodstream quickly, bypassing the liver and the kidneys during the first pass of the metabolism. Although this method of treatment is effective, it is not convenient, and administering the correct dosage can be a challenge given the problems of leakage of the medication outside the body and the interaction with the contents of the bowel. The delivery of the medication and the ability of the medication to stay in the intended location, where it will be most beneficial, has been a challenge.

It is common practice to administer rectal suppositories manually using a finger while the patient is, for example, lying on the left side in the fetal position, and after having emptied the bowel. After insertion of the suppository, patients are instructed to remain on their side in the fetal position for an extended period of time (e.g., at least 30 minutes) while the suppository has time to melt within the anus or rectum, and the body begins the absorption process.

SUMMARY OF THE INVENTION

A method of manufacturing a suppository includes manufacturing the suppository in the presence of and in contact with an element configured to be used to insert the suppository into a cavity of the body.

The element can be a barrel, a plunger, or a combination of a barrel and a plunger. The method may include using the element to define a shape of the suppository during the manufacturing.

The manufacturing can be in the presence of the element, e.g., the barrel or the plunger, in a manner through or around the element or through a gas flow path defined by the element, and can be in contact with an inside or outside of the element.

The suppository can be made from a substance in a liquid, gel, or paste (generally referred to herein as a liquid) or solid form using a molding process. The liquid, gel, paste or solid may be poured, injected, instilled, dropped, or otherwise passed through or around a flow path of one or more of the elements. Manufacturing the suppository can include causing the substance to pass through a mold into contact with the element. In one example, manufacturing the suppository includes manufacturing the suppository from solid pieces that are liquefied and then re-solidified to form the suppository.

In an embodiment, manufacturing the suppository includes forming a sealing engagement between the element and the suppository. The sealing engagement may include one or more surfaces of contact (e.g., one or more points of contact) between the element and the suppository, the surface(s) of contact being configured to hold the suppository in engagement with the element until a user administers the suppository. For example, the element may have a protrusion or an indentation, or may include a hole (e.g., a fill hole), as described elsewhere herein. When the liquid medication or substance solidifies forming the suppository, the medication forms a 'shaped seal' at or with the protrusion, indentation or hole, which prevents the suppository from separating from the element until the user administers the suppository. For example, depending on the cure time and shrinkage of the suppository material, the suppository may fall out of the end of the barrel of the applicator or insertion device before the patient is ready to administer the suppository. This can be prevented by providing the barrel with an indentation or protrusion around which the liquid or other form of medication can mold and solidify during the manufacturing process.

In some embodiments, there is an interconnection between an element, e.g., a barrel, and the suppository that may allow the suppository to slide freely in or out of the element, e.g., the barrel. Alternatively, the arrangement may be such that the suppository is locked within the barrel until advancement of the plunger pushes the suppository out the forward end of the barrel.

The method can include manufacturing a smoothed or non-smoothed suppository with multiple contact surfaces through gas flow path(s).

The shape of the suppository may be determined by one or more of the elements. For example, the element can be the combination of the barrel and plunger, and manufacturing the suppository can include forming a shape of the suppository while the plunger is within the barrel. Further, the combination can be positioned in contact with a wrapper prior to forming the shape of the suppository. A shape of the suppository (e.g., a shape of an end of the suppository) can be formed through use of the wrapper.

The method may include manufacturing the suppository from a front end of the barrel, and can include pre-assembling the barrel with a solid plunger or plunger with a platform end.

The mold that shapes the suppository or a portion of the suppository, such as the tip of the suppository, may be made from steel, wood, plastic, silicone, or other suitable material.

The mold may have flaps that wrap the entire manufactured unit (i.e., applicator-suppository) after curing. The wrapping may be a liner to a mold or it may be the mold itself, shaping the end of the suppository.

In some embodiments, the mold is a convertible mold that provides for multiple mold actions, such as separation of the mold, movement of a solid rod or mold pin, and turning or flipping of the mold.

An embodiment may be in the form of a kit that includes a manufactured unit including a suppository, an element (e.g., a barrel, a plunger or combination thereof) and a wrapper sealed with the element and suppository contained therein, wherein the suppository has a shape that is defined by aspects of the element and the wrapper. The suppository may include a sealing engagement between the suppository and an interior or exterior of the element (barrel, plunger or combination thereof). The element can be configured to be employed to insert the suppository into a cavity of the body. In some embodiments, the element defines a gas flow path and the suppository defines a gas flow path, the gas flow paths being axially or non-axially aligned.

A method includes manufacturing a shaped solid drug suppository from a substance in liquid, gel, powder, or paste form and allowing the proper curing of the substance in the presence of and in contact with an element configured to be used as a part of the administration of the drug.

In certain embodiments, there may be at least two elements. The elements, which need not include a barrel or a plunger, can be configured to fit and work together for the administration of the drug.

The suppository can be manufactured in the presence of any of the elements of the suppository insertion device in a manner through or around any of the elements, and may be in contact with an inside or outside of any of the elements. The suppository may have the same sealing engagement and interconnection as described above.

In certain embodiments, manufacturing the suppository includes manufacturing the suppository in a manner defining a gas flow path therethrough. For example, manufacturing the suppository can include forming a solid suppository and subsequently forming a hole therethrough, the hole defining the gas flow path. The gas flow path may also be molded during the manufacturing of the suppository. In some embodiments, the element defines a gas flow path and the suppository with the gas flow path is manufactured in a manner resulting in an axial alignment between the gas flow paths of the element and the suppository or, alternatively, in a non-axial alignment between the gas flow paths. Manufacturing can also include arranging the suppository and the element to align the gas flow paths of the element and suppository axially, non-axially, or in some other manner that allows for gas flow to be maintained.

The element may be employed to define a shape of the suppository during the manufacturing. Alternatively or in addition, a wrapper may be employed to assist in forming a shape of the suppository, and optionally, the wrapper may be sealed with the element and suppository contained therein. The wrapper can be a liner to a mold or a mold and can be configured to shape and end of the suppository.

Embodiments of the present invention have many benefits. For example, manufacturing suppositories through use of a suppository applicator or insertion device reduces the number of manufacturing and packaging steps to manufacture and package pairs of suppositories and applicators, lowers manufacturing costs, reduces the amount of packaging, and eliminates the multiple steps required by the patient in utilizing the suppository in conjunction with the applicator. The use of the resulting applicator-suppository combination is more hygienic than the use of separate applicator and suppository, which requires handling of the medication. In addition, the use of the resulting applicator-suppository combination provides more efficiency from time of opening the packaging to time of commencing administration of the suppository.

Manufacturing the suppository through the use of the suppository applicator or insertion device eliminates several steps in the manufacturing process, eliminates assembly by the user, and offers an easier to use and more hygienic presentation of a medication. The suppository applicators can be shipped in bulk from the plastics manufacturing facility to the drug manufacturing location. Elements of the suppository applicator, such as a barrels or plungers, can be used to mold the suppository medication. Liquid medication can be poured into one or more elements of the suppository applicator and be allowed to cure. As a result, the applicator and the suppository can be packaged together in one containing unit. The required number of units may be packaged and sold in one box with the instructions for use. When a patient is ready to use the product, no assembly is required. The patient simply opens the box, unwraps a single prefilled unit, and administers the medication according to the instructions for use.

Furthermore, by manufacturing the suppository within the applicator or container, the batch quantity can be reduced to one suppository per batch, which can reduce waste due to incompletely filled or shaped suppositories. In a conventional manufacturing process, suppositories are filled in batches of multiple suppositories per mold or strip. If one of the suppositories is incompletely filled or improperly shaped, the whole batch is typically discarded. In contrast, if one suppository is filled into an applicator or container at a time, any one improperly filled or shaped suppository may not affect the quality of the other suppositories being manufactured, even when manufacturing is performed at high speed. Thus, embodiments of the invention can beneficially reduce waste due to improper filling, overcoming a drawback of standard batch manufacturing processes for suppositories.

Embodiments of the invention can also be applied to cosmetics, such as lipstick, lip balm, and deodorant. In the case of cosmetics, one or more of the elements may or may not include gas flow path(s) since gas flow path(s) may not substantively contribute to proper delivery of the cosmetic, such as a topical cosmetic. However, the gas flow paths may be advantageous for manufacturing of the cosmetic with the elements preassembled prior to pouring the liquid and curing the solid. Manufacturing of cosmetics can also benefit from the reduction in waste offered by embodiments of the invention.

An apparatus and corresponding method for inserting a rectal suppository into an animal or human according to example embodiments includes a hollow barrel to be inserted into an anal canal, the barrel having open proximal and distal ends defining a gas flow path into and out of the body. The example embodiment further includes a hollow plunger, having open proximal and distal ends, to be movably coupled to the barrel with the gas flow path maintained. The example embodiment further includes a hollow rectal suppository, open at both ends, to be loaded in the barrel, maintaining the gas flow path. The plunger is movably extendable past the open end of the barrel to insert the suppository into the rectum while maintaining the gas flow path into and out of the body during insertion of the suppository and withdrawal of the apparatus.

The plunger is configured to insert the suppository above an "anal trigger zone" into the rectum to minimize contact of the suppository with the nerves that trigger contraction of anal sphincter muscles that may affect the body's ability to retain and absorb the medication.

The hollow plunger may include structural elements within the tube that maintain the gas flow path into and out of the body established by the hollow barrel and hollow suppository, both with established open ends.

An alternative example embodiment includes a non-hollow plunger with structural elements, such as fins or spacers, that maintain the gas flow path into and out of the body established by the hollow barrel and hollow suppository, both with established open ends.

In other example embodiments, the suppository can include structural elements that maintain the gas flow path into and out of the body established by the hollow barrel and hollow plunger, both with established open ends. An inactive, and optionally inert, binding agent including, for example, an oil-based fat or a polyethylene glycol, and an active pharmacological ingredient may compose the rectal suppository. The inactive binding agent can be used to contain the active ingredient and define a solid geometrical shape therethrough.

In yet another example embodiment, an apparatus includes a plunger and suppository combination defining a gas flow path and configured to insert the suppository past an anus and into a rectum while maintaining the gas flow path during insertion of the suppository and withdrawal of the plunger out of the rectum and anus. The suppository can be solid and the plunger can include a piston rod configured to push the suppository away from the plunger.

The barrel may be formed by at least two sub-barrels arrangeable to form the barrel, and the plunger may be formed by at least two sub-plungers arrangeable to form the plunger.

Some example embodiments may include a suppository support element configured to support a suppository at least partially below an open end (e.g., insertion end) of the barrel. The plunger may include a suppository interface end that is as wide as, or wider than, a portion of the suppository with which the interface end is configured to contact. Alternatively, the plunger includes a suppository interface end that is narrower than a portion of the suppository with which the interface end is configured to contact.

The plunger may have a distinct insertion end and a distinct hand or finger-interface end, where the plunger has a length that enables a user, self administering the suppository, to push against the hand or finger-interface end with a finger or palm of the hand. The barrel or plunger may be formed from plastic, polycarbonate, epoxy, acrylic, silicon, rubber, polymer, ceramic, metal, glass, wood, paper, or similar such materials.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A-C are illustrations of applicators configured to insert a rectal suppository according to example embodiments of the invention;

FIGS. 5A-5C are diagrams illustrating a process by which a suppository is manufactured from a substance, e.g., a gel or liquid medication, and in the presence of an assembled drug delivery device;

FIGS. 6A-6B are diagrams illustrating a process for manufacturing a suppository in the presence of a plunger that is subsequently married to the barrel by inserting the end of the plunger into the forward end of the barrel;

FIG. 7A is a cross-sectional view of an example barrel having inner and outer rings;

FIG. 7B is a cross-sectional view of an inner ring of a barrel, such as the barrel of FIG. 7A;

FIGS. 7C and 7D are respective cross-sectional and side views of an outer ring of a barrel, such as the barrel of FIG. 7A;

FIG. 7E is a cross-sectional view of the inner ring of FIG. 7B inserted into the outer ring of FIG. 7C to form a barrel, such as the barrel of FIG. 7A;

FIG. 7F illustrates an example plunger that includes a side hole;

FIG. 8A is a cross-sectional view of a plunger that may be used to manufacture a suppository according to an embodiment of the present invention;

FIGS. 8B and 8C are respective side and cross-sectional views of an example barrel that can be used to manufacture a suppository using a plunger such as the plunger described in reference to FIG. 8A;

FIG. 8D is a cross-sectional view of a plunger within a barrel that can be used to manufacture a suppository according to embodiments of the present invention;

FIG. 8E is a side view of the plunger of FIG. 8A including a suppository manufactured through the plunger;

FIGS. 9A through 9D illustrate possible shapes of suppositories manufactured using embodiments of the present invention;

FIGS. 12A-12E are diagrams illustrating example embodiments for manufacturing a shaped suppository from a substance, e.g., a gel or liquid medication, in the presence of a device element and through a void in the element;

FIGS. 16A-16C are diagrams of example molds that can be used to shape the tip of the suppository during manufacturing including curing;

FIGS. 19A-19H are diagrams illustrating an example apparatus and process for manufacturing a suppository using a multiple action convertible mold;

FIGS. 20A-20D illustrate a process for manufacturing a suppository without using a mold;

FIG. 21A is a diagram of a barrel, plunger, and suppository, each of which defining a respective gas flow path according to an embodiment of the present invention;

FIG. 21B is a cross section of the suppository of FIG. 21A;

FIGS. 23A-23D are diagrams illustrating an alternative embodiment of a plunger;

FIGS. 24B-1 and 24B-2 are diagrams of an alternative embodiment of the suppository insertion device of FIG. 24A;

FIGS. 25A-1-25A4 are diagrams of an embodiment of a tip shaping process;

FIGS. 25B-1-25B-4 are diagrams of an alternative embodiment of a tip shaping process;

FIGS. 26A and 26B and 27A-27C are diagrams of another alternative tip shaping process;

DETAILED DESCRIPTION OF THE INVENTION

A description of example embodiments of the invention follows.

The manufacture of suppositories often includes many steps and manual assembly. Typically, the manufacture of suppositories is a molding process whereby a liquid form of a medication or cosmetic is poured into a mold to establish the shape of the solid form. After curing, the solid form is de-molded, packaged into a container or inserted into a device.

One reason for packaging the applicators and suppositories separately within the same box is due to manufacturing processes currently in place. Typically, the applicators and suppositories are manufactured in separate locations. For example, the suppository applicators are manufactured in an injection molding plastics manufacturing facility, while suppository medications are manufactured in a drug manufacturing facility. After manufacturing, the suppository applicators are packaged in required quantities and shipped to the location of the drug manufacturing. Alternatively, the applicators may be shipped to a packaging location, where the suppositories are shipped as well. Currently, some suppositories are molded in a preformed packaging wrap, which is sealed after curing. Others are molded in a steel parting mold and then demolded and packaged. The final box assembly includes the suppository applicators, the suppositories, and instructions for use.

Suppositories typically have a shaped end that is specialized, typically rounded, to facilitate insertion into with the body, which is part of the reason why the suppositories are time consuming or labor intensive to manufacture and load into a suppository applicator.

The multiple steps and arrangement required prior to administration can be difficult for some people with arthritis and other restrictions, necessitating aid from a caregiver or healthcare provider. Furthermore, the patient or caregiver handles the drug prior to administration, leading to a less hygienic administration of the medication. Because suppository medication is designed to melt at body temperature, too much handling can cause the suppository shape to distort, making it difficult to administer.

Figure 1:
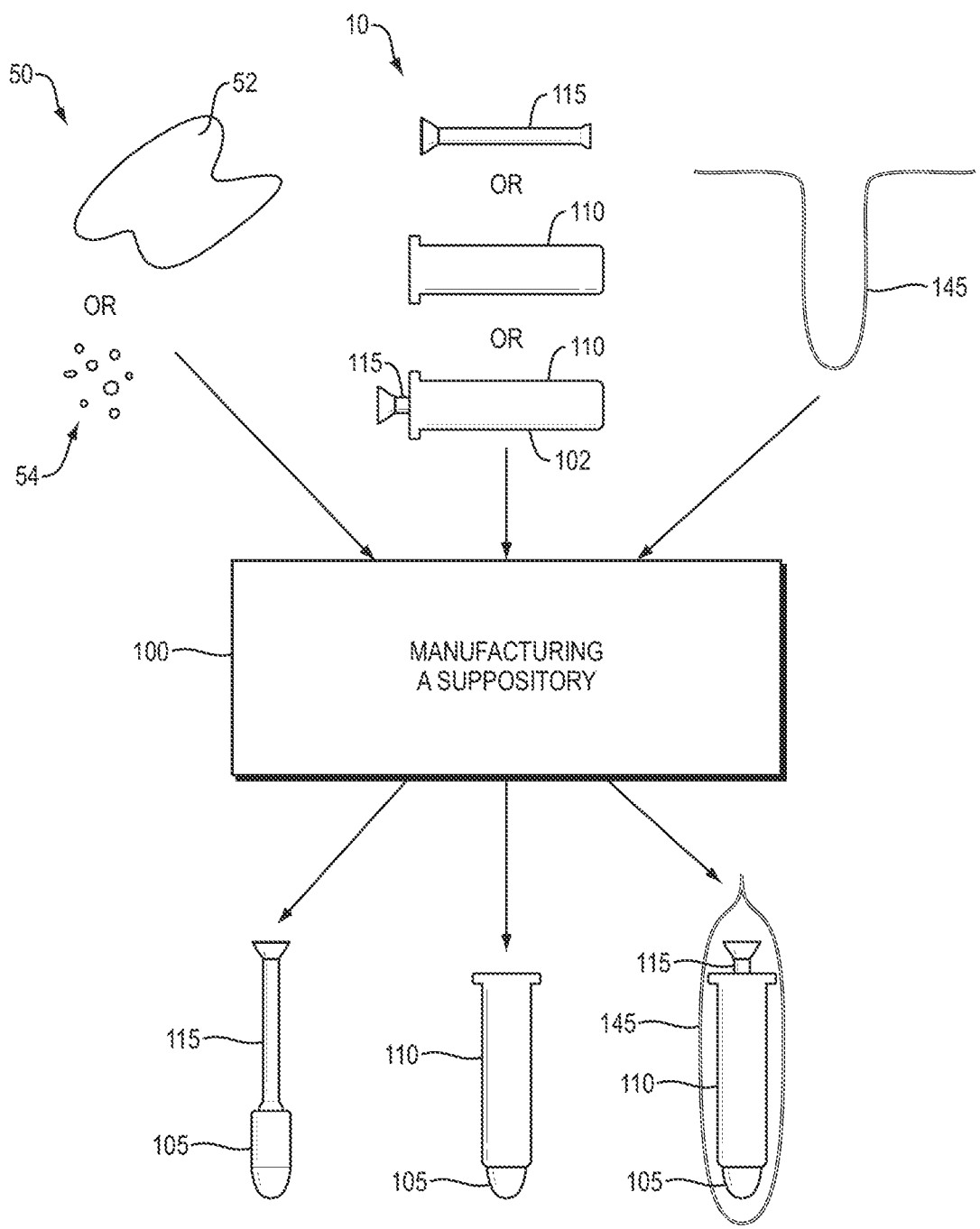
FIG. 1 is a schematic diagram illustrating manufacturing of a suppository in accordance with example embodiments of the invention.

FIG. 1 is a schematic diagram illustrating a method of manufacturing a suppository in accordance with example embodiments of the invention. A suppository 105 is manufactured 100 in the presence of and in contact with one or more elements 10 configured to be used to insert the suppository into a cavity of the body. Each element 10 can be a barrel 110, a plunger 115, or a combination 102 of a barrel and a plunger.

The suppository can be made from a substance 50 using a molding process. The substance 50 can be in a liquid, gel, or paste form (generally referred to herein as a liquid 52) or solid form 54, as schematically illustrated in FIG. 1. The substance 50 may be poured, injected, instilled, dropped, or otherwise passed through or around a flow path of one or more of the elements 10. The manufacturing can be in the presence of the element 10, e.g., the barrel 110 or the plunger 115, in a manner through or around the element or through a gas flow path defined by the element, and can be in contact with an inside or outside of the element. The method may include using the element 10 to define a shape of the suppository 105 during the manufacturing. Alternatively or in addition, the method may include using a wrapper 145, which can be a mold or a liner to a mold, to define a shape of the suppository 105.

Figure 2:
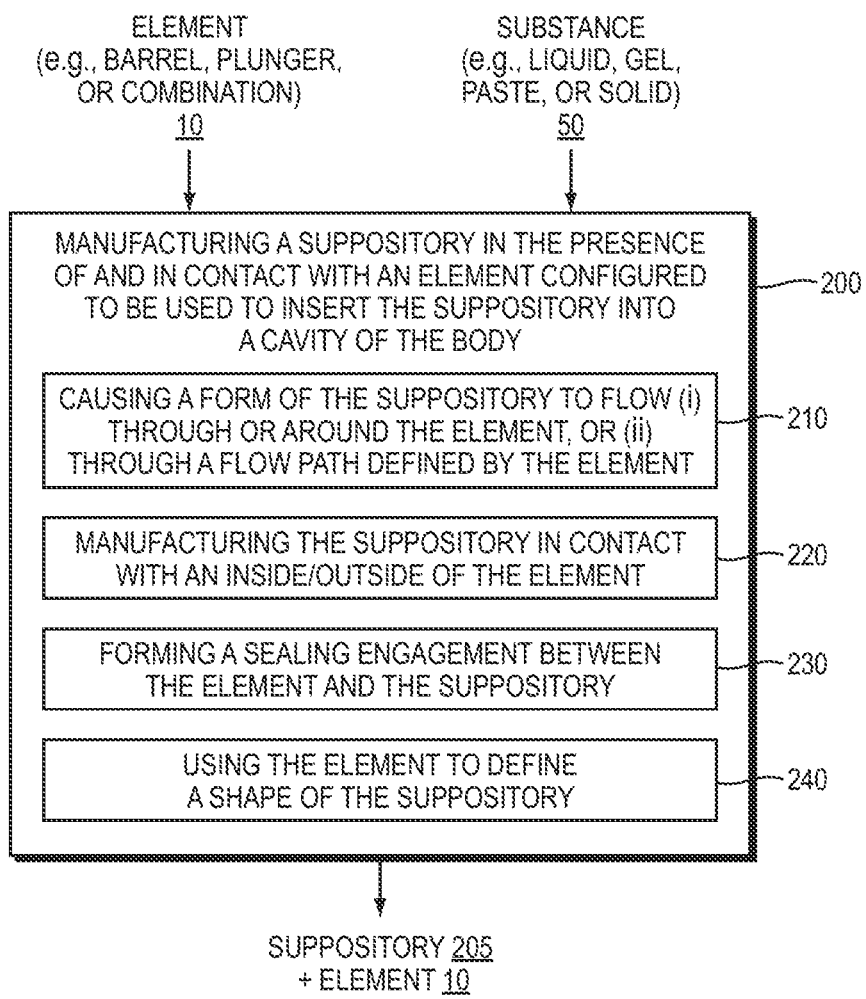
FIG. 2 is a flow diagram illustrating a procedure for manufacturing a suppository performed in accordance with example embodiments of the invention.

FIG. 2 is a flow diagram illustrating a procedure for manufacturing a suppository performed in accordance with example embodiments of the invention. As shown at block 200, a method of manufacturing a suppository includes manufacturing the suppository in the presence of and in contact with an element 10 configured to be used to insert the suppository 205 into a cavity of the body. The element 10 can be a barrel, a plunger, or a combination of a barrel and a plunger. The suppository 105 can be made from a substance 50 in a liquid, gel, paste or solid form using a molding process. As shown at block 210, manufacturing the suppository 205 can include causing a form of the suppository to flow (i) through or around the element 10, or (ii) through a flow path (e.g., gas flow path) defined by the element 10. In general, the a liquid, gel, paste or solid suppository material may be poured, injected, instilled, dropped, or otherwise passed through or around a flow path of one or more of the elements. As shown at block 220, the suppository 205 may be manufactured in contact with an inside or an outside of the element 10. As shown at block 230, manufacturing the suppository 205 can include forming a sealing engagement between the element 10 and the suppository 205. As shown at block 240, manufacturing the suppository may include using the element 10 to define a shape of the suppository 205 during the manufacturing.

It should be readily appreciated by those of ordinary skill in the art that the aforementioned blocks are merely examples and that the present invention is in no way limited to the number of blocks or the ordering of blocks described above. For example, some of the illustrated blocks may be performed in an order other than that which is described or include more or fewer blocks. Moreover, it should be understood that various modifications and changes may be made to one or more blocks without departing from the broader scope of the present invention. It should also be appreciated that not all of the illustrated flow diagram is required to be performed, that additional flow diagram(s) may be added or substituted with other flow diagram(s).

Examples of devices and methods for inserting a suppository are described in U.S. Pat. No. 8,192,393, entitled, "Method And Apparatus For Inserting A Rectal Suppository," issued on Jun. 5, 2012, the entire teachings of which are incorporated herein by reference.

FIG. 3A illustrates an example applicator configured to insert a rectal suppository 305 into a human or animal according to the present invention. The applicator may include a barrel 310 and a plunger 315. The barrel 310 has a gripping end 312 and an insertion end 307 and is appropriately sized and shaped to fit within a patient's anal canal. The barrel 310 is further configured to define a gas flow path 320 allowing gas to freely flow through the barrel 310 when positioned within the anal canal. The plunger 315 is configured to be substantially longer than the barrel, thereby allowing the plunger 315 to extend beyond the end of the barrel 310. For example, the barrel 310 may be approximately 4 cm whereas the plunger may be approximately 8 cm.

Thus, the applicator can be configured to insert a suppository 305 above a patient's anal trigger zone. In doing so, the suppository 305 minimizes contact with nerves that trigger the sphincter muscles that may effect (i.e., reduce) the body's ability to retain and absorb medication provided by the suppository. For example, when a suppository is positioned within the anal trigger zone excessive contact with these nerves may create the urge to release contents within the bowel and, along with these contents, a portion of medication that has been released from the suppository but not yet absorbed by the body. It should be noted that the aforementioned dimensions are merely examples and are not meant to be limiting and alternative dimensions may be similarly used such that the plunger 315 extends beyond the barrel 310.

The plunger 315 may be configured to be movably or slidably coupled to the barrel 310 and is further configured to maintain a second gas flow path 325 that allows gas to freely flow through the plunger 315 as the plunger is withdrawn from the rectum and anal canal after the suppository 305 has been inserted to a desired position. Thus, as the suppository 305 is being inserted, the barrel 310 maintains a gas flow path 320 allowing gas to escape. As the plunger 315 is being withdrawn, the plunger's gas flow path 325 and the barrel's gas flow path 320 are maintained as the plunger is withdrawn from the suppository 305 and the barrel 310 and plunger 315 are removed from the patient's anal canal. The gas flow paths, 325 and 320 allow gas to escape as the barrel 310 and the plunger 315 are removed from the body preventing or reducing the need to release the gas in the form of flatulence.

FIGS. 3B and 3C illustrate end views of an applicator that further includes at least one gas flow path spacing element 330, 335 configured to maintain the barrel's 310 gas flow path 320. Referring to FIG. 3B, the barrel 310 includes the at least one gas flow path spacing element 330 where the spacing element extends inward from an inner wall of the barrel 310 to contact the outer wall of the plunger 315, thereby maintaining barrel's gas flow path 320. Since the plunger 315 is hollow, a second gas flow path 325 is maintained within the plunger 315 as well. FIG. 3C illustrates an alternative example applicator where the at least one gas flow path spacing element 335 extends outward from an outer wall of the plunger 315 to contact an inner wall of the barrel 310 to maintain the barrel's gas flow path 320. Also shown is the at least one second gas flow path 325 maintained by a similarly hollow plunger 315. Alternatively, at least two gas flow path spacing elements may simultaneously extend inward from the inner surface of the barrel 310 and outward from the outer surface of the plunger 315 to maintain the first gas flow path 320.

Figure 4A:
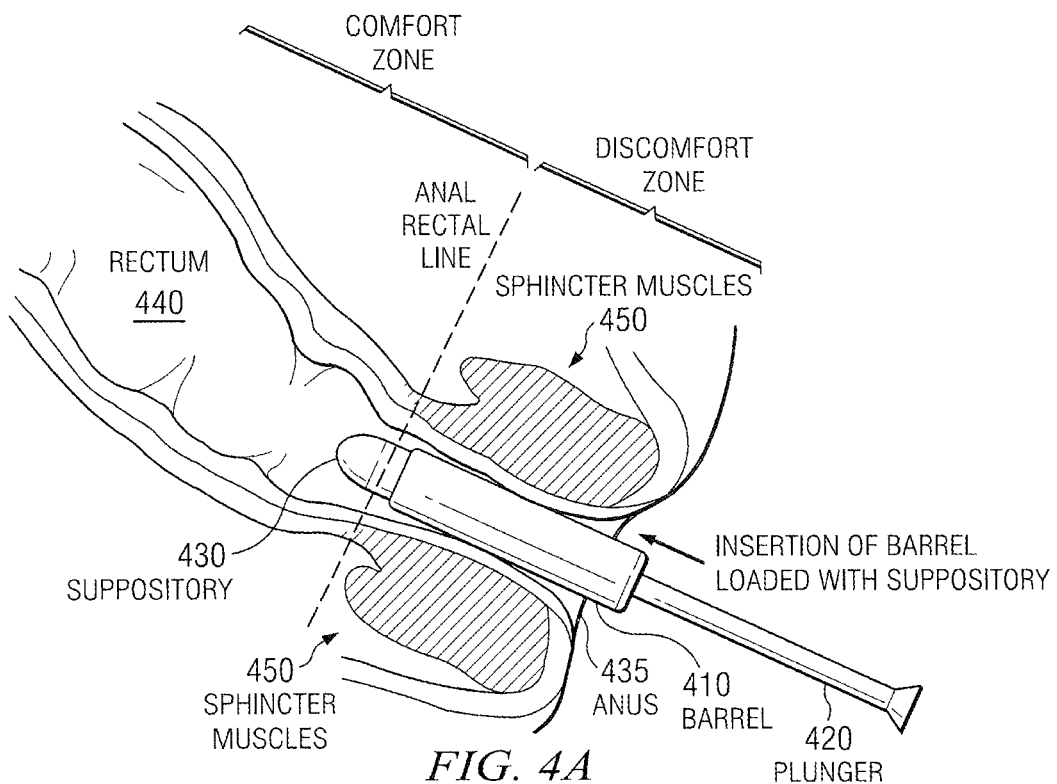
FIGS. 4A-C are anatomical diagrams illustrating an example embodiment of the invention in various states of use.
Figure 4B:
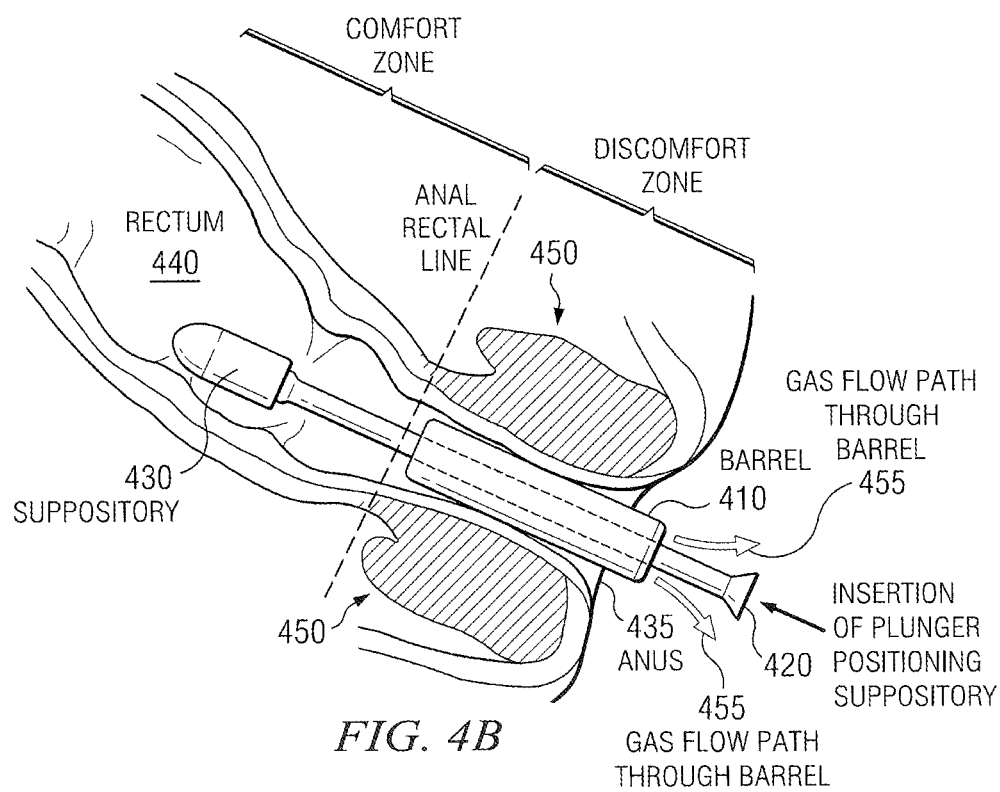
Figure 4C:
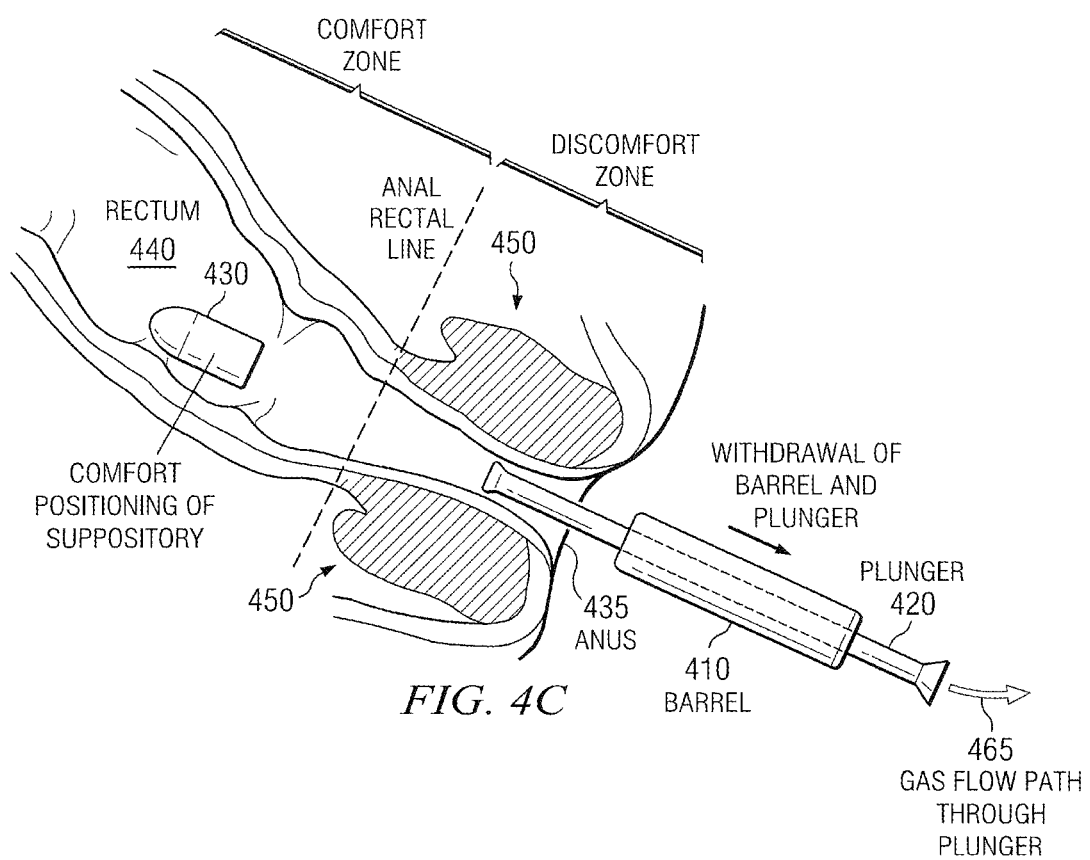

FIGS. 4A-C illustrate employing an applicator to insert a suppository 430 into a patient's rectum 440 in varying states of use. The applicator may include a barrel 410 and a plunger 420. Referring to FIG. 4A, the plunger 420 is positioned within the barrel and the suppository 430 is loaded into the barrel 410. The applicator is then inserted into the patient's anus 435. Referring to FIG. 4B, the plunger is depressed such that the suppository 430 is inserted within the rectum 440 to a desired position, such as a location within a comfort zone above the patient's sphincter muscles 450 (i.e., above an anal trigger zone). As the plunger 420 is inserted or pushed into the barrel, the barrel 410 maintains a first gas flow 455 such that any trapped air may escape through the barrel 410 to outside the patient's anus 435. Referring now to FIG. 4C, once the suppository has been positioned in the desired location, the applicator may be removed from the patient's rectum 440. As the plunger 420 is removed, suction effects due to withdrawal of the plunger 420 are prevented by venting any pressure or vacuum buildup through the second gas flow path 465 maintained by the plunger 420.

The examples illustrated in FIGS. 3A-C and 4A-C are examples of a plunger and barrel configured to maintain a first and second gas flow path. However, numerous other barrel and plunger configurations are envisioned where a first and second gas flow path are maintained within the barrel and plunger, respectively. Furthermore, the suppository may define a gas flow path as described elsewhere herein.

An embodiment of the invention is a process of manufacturing a suppository medication within a drug delivery device that eliminates the arrangement of a suppository and suppository applicator (sometimes referred to herein as components) by the patient or caregiver prior to administration of the suppository. The suppository manufacturing process can be accomplished prior to or after assembly of the drug delivery device and in the presence of one or more elements of the device. After a liquid medication has been poured into association with an element of the suppository applicator, the liquid medication is allowed to cure. After curing, the prefilled device and suppository combination can be packaged as a single unit.

FIGS. 5A-5C are diagrams illustrating a process by which a suppository 505 is manufactured from a substance, e.g., a gel or liquid medication, and in the presence of an assembled drug delivery device 502. As shown in FIG. 5A, a delivery device 502 is pre-assembled and the substance is filled or poured into the assembled device. In this and subsequent figures, arrows and the word "Fill" are used to illustrate the process of filling, pouring, or otherwise causing the substance to flow into an element that is configured for insertion of the suppository. After filling, a curing process completes manufacturing of the prefilled unit.

In some embodiments, the substance, e.g., gel or liquid medication, can be poured within the barrel of the device, and the plunger can be assembled with the barrel-suppository combination after the curing process, a description of which is provided below in reference to FIG. 11B. Alternatively, the substance can be filled in a mold in contact with the plunger, and, after the curing process is complete, the plunger-suppository combination can be married with the barrel to complete the assembly, a description of which is provided below with reference to FIG. 6B.

As shown in FIGS. 5A and 5B, the assembled device 502 can include a barrel 510 and a plunger 515 positioned inside the barrel 510. In the example shown, the barrel 510 includes fins 530 extending into the inside of the barrel along a length of the barrel. The barrel 530 includes a void space 532, e.g., a space free of fins, to hold the suppository. The fins 530 provide gas flow paths 520 that contribute to proper delivery of the suppository. The fins 530 are similar to the spacing elements 330, 335 described above in reference to FIGS. 3B and 3C. Alternatively, the fins may extend from the plunger as for example shown in FIG. 3C. Elements (barrels/plungers) need not have fins to define gas flow paths or void spaces, but can have other characteristics or features that define areas of a void or a gas flow path. Examples of plungers having fins or other features, such as cut-out areas, that can establish gas flow paths are described in U.S. Pat. No. 8,192,393, the relevant teachings of which are incorporated herein by reference.

FIG. 5C illustrates the insertion device 502 sitting in a suppository mold 540 and being filled with liquid medication for manufacturing the suppository 505. The mold 540 can be used for setting the shape of the suppository end. The mold may include a liner, such as the liners described in reference to FIGS. 17A-18B.

As shown in FIG. 5C and also FIG. 5A, manufacturing can include pouring liquid medication through an end 517 of a hollow plunger 515, one or more gas flow paths 520 in the barrel 510, a hole 535 in the barrel that provides access to a gas flow path (e.g., a gas flow path between fins 530), or any combination thereof.

FIGS. 6A-6B are diagrams illustrating the manufacturing of a suppository 605 in the presence of a plunger 615 that is subsequently married to the barrel 610 by inserting an end 617 of the plunger into the forward end (insertion end 614) of the barrel.

As shown in FIG. 6A, manufacturing the suppository 605 can include pouring a substance in liquid form through open end 617 of hollow plunger 615, a fill hole 635 in a side of the plunger, or a space outside of the plunger between the plunger and the mold e.g., near the insertion end 619 of the plunger. A support 618 may be used to support the plunger 615 at a specific height above mold 640. The plunger may be supported until the curing of the suppository 605 is complete. As shown, there is a surface of contact 613, which can be a contact point, between the plunger 615 and the suppository 605. Manufacturing can include deforming the suppository 605 around the contact surface or contact point, or allowing curing of the suppository around the contact surface or contact point to facilitate de-molding the plunger 615 and suppository 605 combination. In some embodiments, there may be more than one contact surface or contact point.

As shown in FIG. 6B, the plunger 615 and suppository 605 combination of FIG. 6A can be married to the barrel 610 of the insertion device by inserting the back end 617 of the plunger into the forward end 614 of the barrel 610. The barrel 610 may have fins as described above. The fins 630 can create a stop 631 within the barrel, which limits depth of insertion of the plunger and suppository combination into the barrel. Upon insertion of the plunger 615 and suppository 605 combination into the barrel 610, one end of the suppository 605 sits at the stop 631 formed by the fins 630. Also, as described above in reference to FIG. 5A, fins to establish gas flow paths may extend from the plunger.

Figure 7C:
FIGS. 7A-7F and 8A-8E are diagrams of example elements of insertion devices, which may be used in a process for manufacturing a suppository.
Figure 7F:
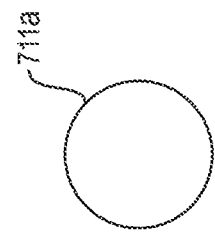
Figure 7B:
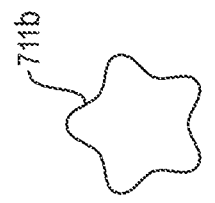
Figure 7E:
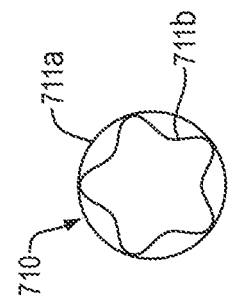
Figure 7A:
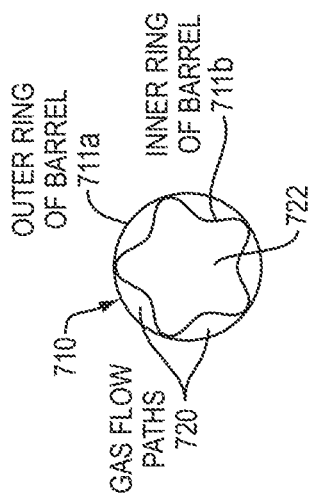

FIGS. 7A-7F are diagrams of elements of an example insertion device. The elements or components of the device, i.e., the barrel and the plunger, can help to define the shape of the suppository. For example, a barrel 710 may have a shape that is defined by an outer ring 711*a* attached to an inner ring 711*b* of a different shape than the outer ring as illustrated in FIG. 7A. The space 722 allowed within an inside of the inner ring 711*b* can be used to hold and cure a liquid medication. In addition, the space between an outside of the inner ring 711*b* and an inside of the outer ring 711*a* can define one or more gas flow paths 720 of the barrel element. The barrel and the plunger of the device may be made of plastic, wood, cardboard or any combination of materials. If the elements are made of plastic, they may be injection molded or extruded as illustrated in FIGS. 7B-7E.

The embodiments shown in FIGS. 7A-7F are useful for manufacturing a shaped suppository whose beneficial features can include multiple contact surfaces and increased surface area.

Figure 7D:
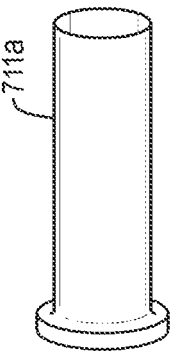

FIG. 7B is a cross-sectional view of an inner ring or inner barrel 711*b*, which may be made of extruded plastic. FIGS. 7C and 7D are respective cross-sectional and side views of an outer ring or outer barrel 711*a*, which may be made of injection-molded or extruded plastic.

FIG. 7E is a cross-sectional view of the inner ring 711*b* of FIG. 7B inserted into the outer ring 711*a* of FIG. 7C to form a barrel 710, such as the barrel of FIG. 7A. Alternatively, a barrel having the cross-section shown in FIG. 7E can be formed in one piece, for example by extruding the inner and outer rings together.

FIG. 7F illustrates an example extruded plastic plunger 715 having a side hole 735 added later, i.e., via secondary tooling, to allow filling with a medication or to allow air flow. Any of the elements described herein may have secondary tooling to define the shape of the elements further. Also, the elements may have an addition of a secondary part or parts, which may be made in a different manner or of a different material from the elements themselves.

In some embodiments, the plunger may include multiple pieces similar to the barrel shown in FIGS. 7A-7E. The plunger may include an inner piece, or inner ring, and an outer piece, or outer ring. The pieces or rings may differ in shape. For example, the plunger may include an extruded inner piece that has a non-circular shape and that is inserted into an extruded or injection-molded outer piece that is round in shape. Alternatively, the plunger may have an outer wall that is star shaped and an inner wall that is round, i.e. circular, in shape. The plunger can be placed or inserted into a round shaped, i.e. circular, barrel. Examples of such plungers and barrels are described in reference to FIGS. 8A-8E. In the examples shown, liquid medication can be filled through one or more spaces or voids between the inner and outer shapes. The star shape of the plunger in contact with the round shape of the inner wall of the barrel would allow gas flow. Further, liquid medication can be filled or poured into, around, or in contact with the plunger, and may be poured within the inner shape of the plunger. In addition, by preventing the liquid to fill the space between the two pieces of the plunger, embodiments can provide for a gas flow path through the plunger.

Figures 8A, 8B, 8C, 8D, 8E:
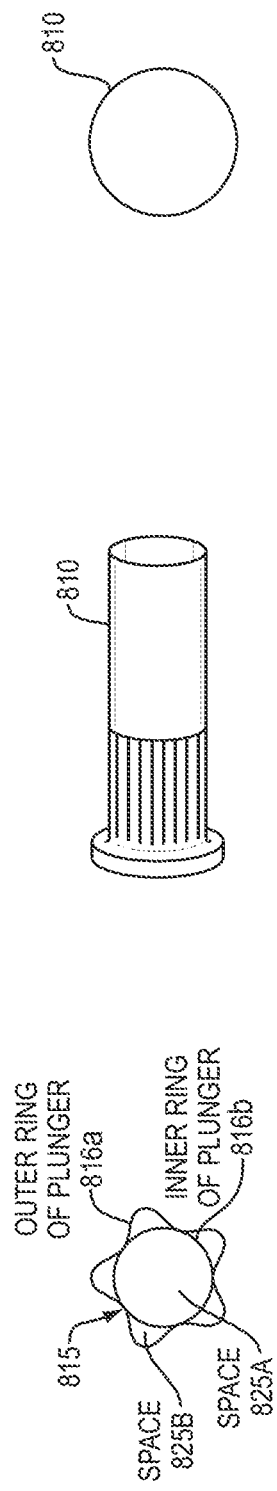

FIG. 8A is a cross-sectional view of a plunger 815 that may be used to manufacture a suppository according to an embodiment of the present invention. The plunger includes an inner ring 816b and outer ring 816a, the inner ring being disposed inside the outer ring. The inner ring defines a space or void inside the inner ring, shown as space 825A in FIG. 8A. Fortunately, the inner ring and outer ring define one or more spaces or voids between the inner ring and the outer ring of the plunger, shown as space 825B in FIG. 8A. In one example (Option A), the suppository is manufactured through space 825A of the plunger. For example, manufacturing includes filling a liquid medication through the void or space defined by the inner ring (space 825A in FIG. 8A). In this example, space 825B offers a path for gas flow (e.g., air flow) through the plunger. In another example (Option B), the suppository is manufactured through spaces 825A and 825B. For example, liquid medication is filled or poured into the plunger through spaces 825A and 825B. In this example, gas flow can be allowed through a void or space between the outer ring of the plunger outer ring and a barrel.

FIGS. 8B and 8C are respective side and cross-sectional views of an example barrel 810 that can be used to manufacture the suppository using a plunger, such as the plunger 815 described in reference to FIG. 8A. Possible gas flow paths through a device that includes a plunger inside a barrel are described in reference to FIG. 8D.

FIG. 8D is a cross-sectional view of a plunger 815 within a barrel 810 that can be used in the method of manufacturing a suppository according to embodiments of the present invention. As shown, the plunger 815 includes an inner ring 816b inside an outer ring 816a, as discussed in reference to FIG. 8A. The plunger 815 defines possible gas flow paths 825 between the inner and the outer ring. Furthermore, additional gas flow paths 820 can be provided between the outer ring 816a of the plunger and an inside of the barrel 810. Manufacturing the suppository using the plunger and barrel combination shown in FIG. 8D may be accomplished, for example, via the two manufacturing options (Option A, Option B) described above in reference to FIG. 8A.

FIG. 8E is a side view of a plunger 815, such as the plunger described in reference to FIG. 8A, including a suppository 805 manufactured through the plunger. As shown, the tip 806 of the suppository extends beyond the distal end (insertion end) 819 of the plunger.

FIGS. 9A through 9D illustrate possible shapes of suppositories manufactured using embodiments of the present invention. The figures illustrate possible shapes of suppositories 905a, 905b that can be manufactured using, for example, the barrels or plungers described in reference to FIGS. 8A through 8E. It will be understood that the embodiments of FIGS. 9A through 9D are merely examples of possible shapes of suppositories, and that suppositories of other shapes can be manufactured through, around, or in connection with plungers, barrels, or combinations of plungers and barrels that are described herein.

FIGS. 9A and 9C are respective cross-sectional and side views of a suppository 903a manufactured through a space or void in a plunger, such as space 825B shown in FIG. 8A.

FIGS. 9B and 9D are respective cross-sectional and side views of a suppository 905b that has been manufactured through a space between an inner ring and outer ring of the plunger, shown as space 825B of the plunger shown in FIG. 8A.

In some embodiments, the suppository is manufactured to have a sealing engagement between the suppository and one or more elements of the drug delivery device. The sealing engagement can include one or more surfaces of contact, e.g. contact points between the element and the suppository. The contact surfaces or contact points can be on an outside or an inner side of a device element, e.g., on an inside or outside of the barrel or the plunger. The contact surfaces or points can facilitate de-molding of the suppository and can prevent the suppository from falling out of or otherwise separating from the insertion device prior to use by the patient.

When inserted into a body cavity, suppositories with sealing engagements will naturally release from the element, e.g., the plunger, as the suppository warms up to body temperature and the plunger begins to be withdrawn.

Figure 10C:
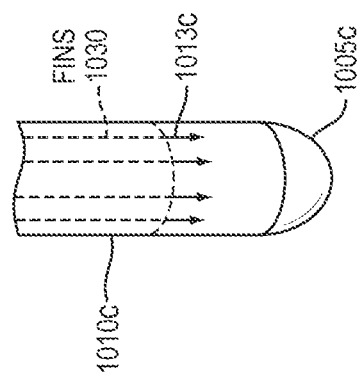
FIGS. 10B-10C are diagrams of suppositories manufactured in the presence of elements configured for insertions of the suppositories and including contact surfaces on the inside of the elements.
Figure 10B:
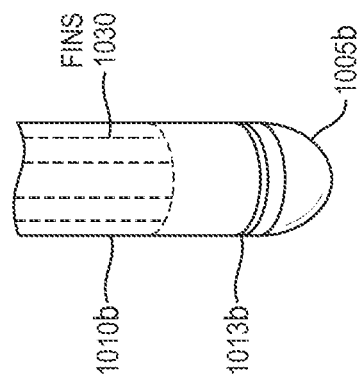
Figure 10A:
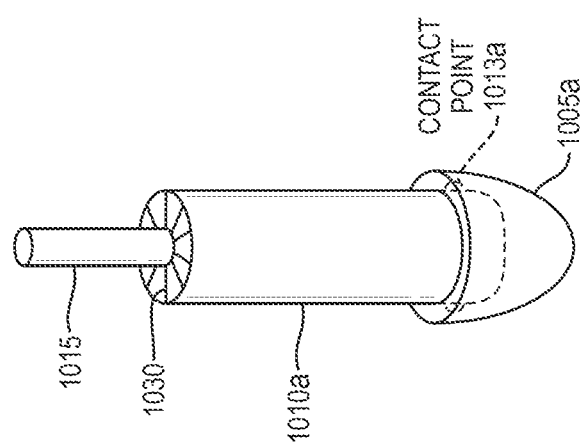
FIG. 10A is a diagram of a suppository manufactured in the presence of an element configured for insertion of the suppository and including a surface of contact on the outside of the element.

FIG. 10A is a diagram of a suppository 1005a manufactured in the presence of an element configured for insertion of the suppository and including a contact point on an outside of the element. As shown, the suppository 1005a is manufactured to the outside of the barrel 1010a and includes a contact surface or point 1013a between the outside of the barrel 1010a and the suppository 1005a. The insertion device, which includes the barrel 1010a and a plunger 1015, can be pre-assembled prior to manufacturing of the suppository.

As shown in FIG. 10A, the contact point 1013a can be a protrusion on the outside wall of the barrel 1010a. Alternatively, the contact point can be an indentation in the wall of barrel. When the liquid medication or substance solidifies forming the suppository, the medication forms a 'shaped seal' with the protrusion or indentation that prevents the suppository 1005a from separating from the barrel 1010 until the user administers the suppository.

FIGS. 10B-10C are diagrams of example suppositories that are manufactured in the presence of elements (1010b, 1010c) configured for insertion of the suppositories and that include contact points on the inside of the elements. As shown in FIG. 10B, the element is a barrel 1010b that includes fins 1030 extending into the inside of the barrel. The suppository 1005b is manufactured to the inside of the barrel. A surface of contact, e.g., contact point, between the suppository 1005b and the barrel 1010b is located on the inside of the barrel, as shown at 1013b. Alternatively or in addition, there can be one ore more contact points 1013c between the suppository 1005c and the fins 1030 that extend into the inside of the barrel, as illustrated in FIG. 10C. The contact points 1013b, 1013c can prevent the suppository from falling out of the barrel during and after the manufacturing process, for example, when a user is handling the suppository-device combination prior to administration of the suppository.

In any of the embodiments shown in FIGS. 10A-10C, the liquid medication or substance is placed proximate to the one or more surfaces of contact or contact points 1013a, 1013b, 1013c in order to ensure the proper sealing engagement of the medication or substance to the element of the device. Manufacturing a suppository according to embodiments of FIGS. 10A-10C typically includes using a mold, which may be any of the molds described herein, including those described in reference to FIGS. 5C, 6A, 12B-12E, 13C-13D, 14B-14C, 15B-15C, 16A-16C, 17A-17B, 18A-18B and 19A-19K.

Figure 11C:
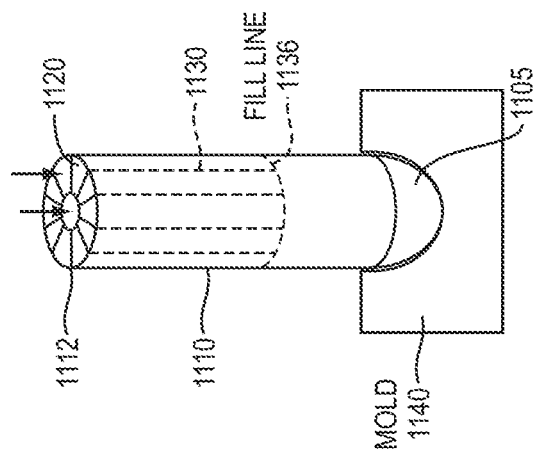
FIGS. 11A-11C are diagrams illustrating example embodiments for manufacturing a suppository from a substance, e.g., a gel or liquid medication, in the presence of a device element and through a gas flow path.
Figure 11B:
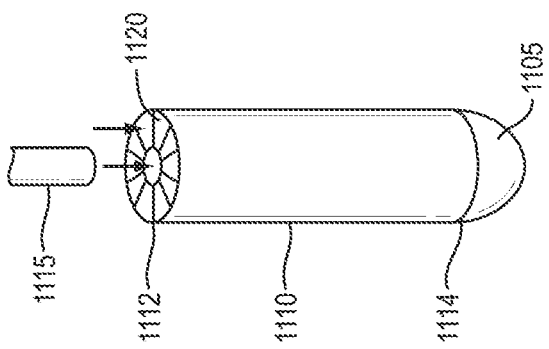
Figure 11A:
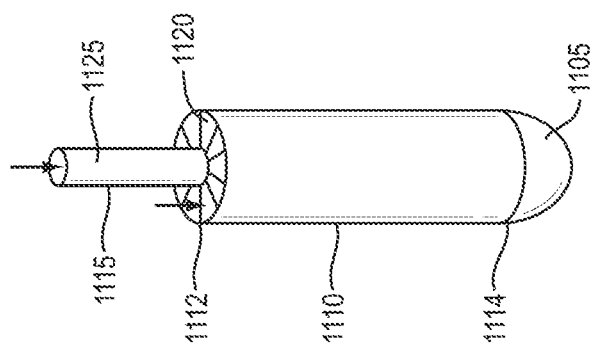

FIGS. 11A-11C are diagrams illustrating example embodiments for manufacturing a suppository from a substance, e.g., a liquid medication in the presence of a device element and through a gas flow path. The substance, e.g., liquid medication, can be poured, dropped, or injected into or around one or more of the device elements 1110, 1115 through one or more of the gas flow paths established by the device elements.

As shown in FIG. 11A, the liquid medication can be filled through one or more gas flow paths 1120, 1125 with the device pre-assembled, i.e., with the plunger 1115 assembled within the barrel 1110. In the example shown, the substance is filled into the barrel 1110 from a proximal end 1112 (interface end) of the barrel in a direction toward the distal end 1114 (insertion end) of the barrel.

As shown in FIG. 11B, the liquid medication can be filled through one or more gas flow paths 1120 before assembly of the device, i.e., without the plunger 1115 in place. The plunger 1115 can then be assembled with the barrel 1110 after filling.

In the example embodiment illustrated in FIG. 11C, manufacturing of the suppository includes filling a substance, e.g., liquid medication, through gas flow paths 1120 of the barrel element 1110. The gas flow paths are defined by the spaces between the inner guides or fins 1130 on the inside of the barrel 1110. The guides or fins 1130 may extend from end 1612 along a length of the barrel 1110 up to a fill line 1136. In order to create the shape of the suppository, the barrel is placed inside or in contact with a mold base 1140 that has a rounded or bullet shaped tip end for the liquid medication to cure to the final shape. After curing, the suppository 1105 and device element 1110 combination can be de-molded and packaged.

FIGS. 12A-12E are diagrams illustrating example embodiments for manufacturing a shaped suppository from a substance, e.g., a liquid medication, in the presence of a device element and through a void in the element. As shown, liquid is poured or filled through the void in the barrel and into a mold. A plunger may be inserted through the void after the liquid medication has solidified.

FIG. 12A shows a cross-section of a barrel 1210 having an inner ring 1211*b* disposed in an outer ring 1211*a* for manufacturing a shaped suppository, similar to the embodiment described above in reference to FIG. 7A. A liquid medication can be poured into the barrel 1210 through the center or void 1222, as shown in FIG. 12A. The manufacturing here is through the void 1222 in the barrel 1210 that will later accommodate a plunger. Depending on the design of the plunger, there can be a gas flow path through the void 1222.

To create a shaped suppository, a suppository mold can include an element or a mechanism that prevents the liquid from reaching and filling the area of the gas flow path. FIG. 12B is a side view of a mold 1240 and a device that includes a barrel 1210. In the example shown, the mold 1240 includes movable mold pins 1242 that extend up into the gas flow paths of the barrel 1210 to prevent filling in the area of the barrel that is indicated by hatching in FIG. 12B, thereby creating the shape of the suppository. As shown, filling can occur through a void 1222 in the barrel 1210. In the example shown, the void 1222 extends along a central axis of the barrel 1210.

FIG. 12C is a side view of a barrel 1210 of an insertion device and a mold 1240 that includes one or more elements that prevent liquid medication from filling gas flow paths of the barrel. This figure illustrates the use of slides 1246 and, in the alternative, the use of mold pins 1244 as barrier elements that prevent the liquid from filling the gas flow paths. Further description of slides and mold pins is provided below with reference to FIGS. 12D and 12E, respectively. Slides and mold pins can be used to manufacture a shaped suppository, such as the suppository shown in FIGS. 9B and 9D. As shown, a liner 1245 may optionally be used to line the mold 1240. The liner 1245 may be a membrane or skim coat of suitable material applied to the mold. Example liners and membranes are described in reference to FIGS. 16A-16C, 17A-17B and 18A-18B.

FIG. 12D is a side view of a barrel 1210 of an insertion device and a mold 1240 including a slide as a barrier element. In this embodiment, one or more slides or barriers 1246 extend into an area of the barrel 1210. The slides prevent the liquid from reaching and filling in the area of the gas flow paths below the fill line 1236. As shown, filling of liquid into the mold base 1240 can occur through a void 1222 in the barrel. The slides or barriers 1246 are removed after the medicine solidifies.

FIG. 12E is a side view of a barrel 1210 of an insertion device and a mold 1240 including mold pins 1244 as barrier elements. The mold 1240 is a multi-part, action mold that includes a mold base 1240 and an upper part 1250. The upper part 1250 of the mold includes or is coupled to pins 1244 that extend into the flow paths of the barrel 1210. The pins 1244 are movable with respect to the barrel 1210 and the mold base 1240. The pins 1244 are supported at a height above the mold base 1240 that is determined by the action of the upper part 1250 of the mold, which, in turn, determines how far the pins 1244 extend into the barrel 1210. The bottom ends 1248 of the mold pins are shaped, e.g., sloped, curved, or rounded, and contribute to shape the suppository. As shown in FIG. 12E, the mold pins 1244 block the filling of liquid medication into the gas flow paths of the barrel 1210. Filling is accomplished through the void 1222 in the barrel 1210, which, as shown, is located in the center of the barrel. The actions or movements of the mold pins 1244 can include at least two steps. First, before the filling of the barrel and mold with the liquid suppository material, the mold pins 1244 move into the gas flow paths to seal the gas flow paths, thereby preventing the liquid from entering the area of the gas flow paths. Second, after the filling and solidification of the suppository material, the mold pins 1244 retract, leaving the molded, solidified suppository in place in the barrel 1210, and in a desired relation to the barrel, to allow gas flow through gas flow paths. Optionally, cooling may be included during the mold actions to reduce cycle time, thereby increasing speed of manufacturing. A description of cooling a mold during the manufacturing process is proved below in reference to FIGS. 19I-19K.

As shown in FIG. 12E, the mold pins 1244 that extend into the barrel 1210 are sloped at the bottom 1248, allowing for a shape of the suppository that is rounded at the back end of the suppository. The shape offers more surface area, which may offer a beneficial therapeutic effect. The rounded shape at the back end of the suppository may also offer a comfort shape that can contribute to increased acceptance by the patient, as compared to standard suppositories, which are typically bullet shaped and include a flat back end.

FIGS. 13A-13D are diagrams illustrating an example process of manufacturing a suppository from a front end (insertion end) of a barrel. In a first step, as shown in FIG.

13A, a substance, such as a liquid medicine, is poured into the barrel 1310 from the front end (insertion end) 1314 of the barrel. Moveable pins 1344 placed in each gas flow path of the barrel 1310 prevent the liquid medicine from filling in the gas flow paths. The pins 1344, which are supported by a support 1350, provide a tight seal during manufacturing of the suppository. As shown in FIG. 13A, the pins 1344 are flush to the same point.

Figure 13B:
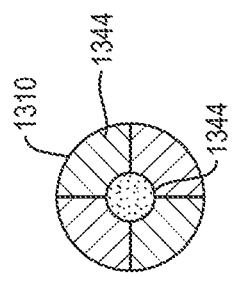
FIGS. 13A-13D are diagrams illustrating an example process of manufacturing a suppository from a front end of a barrel.
Figure 13D:
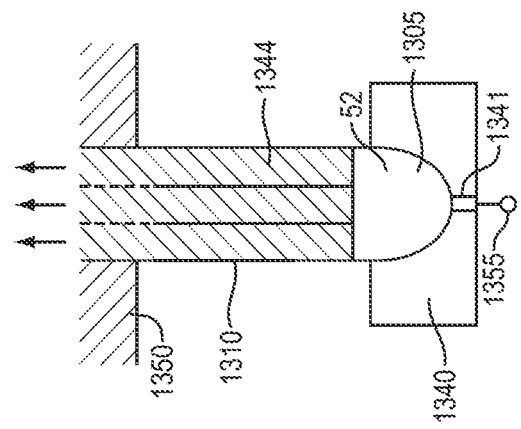
Figure 13A:
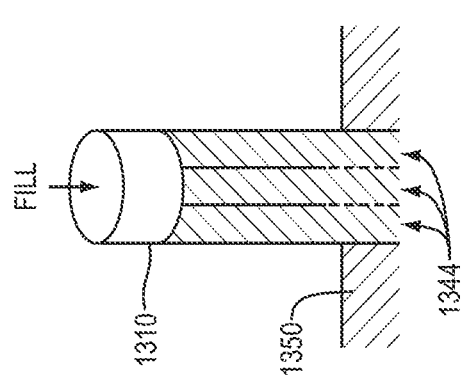

FIG. 13B is a cross-sectional view of the device of FIG. 13A and illustrates the outline of the element, i.e., the barrel 1310, and the mold pins 1344, which are shown as shaded areas. The mold pins 1344 are flush at the same level within the barrel 1310, as shown in FIG. 13A.

Figure 13C:
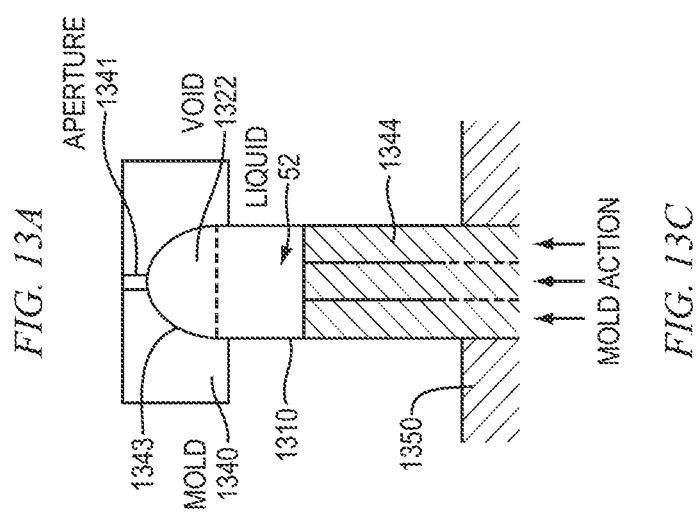

In a second step, as shown in FIG. 13C, the mold base 1340 for the suppository tip is positioned against, and optionally coupled to or attached to, the top forward end (insertion end) of the barrel 1310, after the liquid medication 52 has been poured or otherwise filled into the barrel 1310. The mold base 1340 can have a rounded or bullet shaped portion 1343 to form the tip end of the suppository. The mold 1340 has an aperture 1341. In the orientation of the mold 1340 as shown in FIG. 13C, the aperture 1341 is located at the top and allows air or gas to escape from the void 1322 between the level of the liquid medication 52 and the inner side of the top of the mold 1340. Initially, there is a void 1322 above the liquid medicine in the barrel. A mold action can move the mold pins 1344 up, as indicated by the arrows in FIG. 13C, letting the gas escape from the top void 1322 as the liquid 52 is caused to move up into the mold 1340 by the movement of the mold pins.

In a third step, a pin 1355 is inserted into the aperture 1341 in the mold 1340 to close the aperture. In a fourth step, with the aperture 1341 closed by pin 1355, the mold 1340, suppository 1305, and device (barrel 1310) are flipped, as shown in FIG. 13D, and the mold pins 1344 are retracted, as indicated by the arrows in FIG. 13D. In a fifth step, the suppository 1305 is allowed to cure.

The actions of the mold in the example process illustrated in and described with reference to FIGS. 13A-13D can be fast. For example, retraction of the mold pins 1344 in the fourth step will allow the suppository material, e.g., liquid 52, to settle before curing.

Figure 14C:
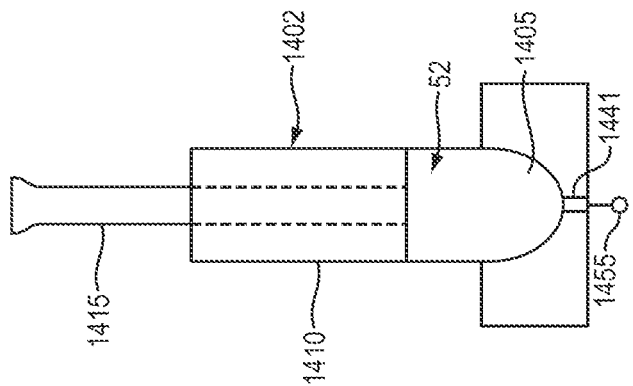
FIGS. 14A-14C are diagrams illustrating other embodiments of a process of manufacturing a suppository from a front end of a barrel.
Figure 14B:
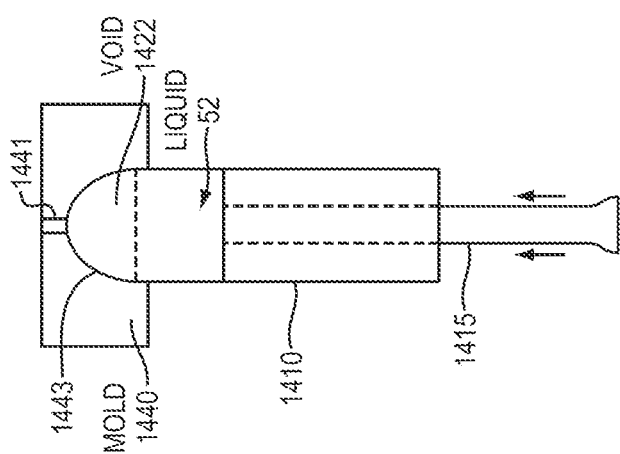
Figure 14A:
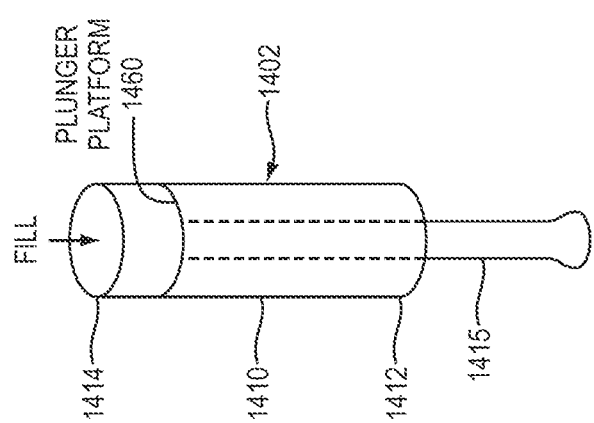

Alternatively, the suppository medication can be manufactured into the drug delivery device without using a gas flow path of the delivery device for filling. FIGS. 14A-14C are diagrams illustrating embodiments of a process of manufacturing a suppository from a front end of a barrel.

As shown in FIG. 14A, a device 1402, including a barrel 1410 preassembled with a plunger 1415, is held upright during the first half of the manufacturing process. The plunger 1415 can be solid or formed with a platform base 1460, as shown. The plunger 1415 is kept at a level low enough to allow for the proper dose of liquid medication to be filled into the forward end (insertion end) 1414 of the barrel 1410. As shown an end of the plunger extends out the proximal end (interface end) 1412 of the barrel. After the liquid medication has been poured or otherwise filled into the barrel 1410, a mold 1440 having a rounded or bullet shaped tip end 1443 is positioned over, and is optionally coupled to or attached to, the top forward end (insertion end) 1414 of the barrel as illustrated in FIG. 14B. Alternatively, or in addition, the filled unit (barrel 1410) can be placed up into the mold 1440 via a manual or automated process. The mold 1440 (also referred herein as a mold base) has an aperture 1441 that allows the escape of air or other gas from the void 1422 between the level of the liquid medication 52 and the inner side of the top of the mold 1440. A mold action at the end of the plunger 1415 advances the solid plunger, or plunger with platform 1460, up (indicated by arrows in FIG. 14B), to push the liquid 52 into the mold 1440 and any gas (e.g., air) within the void 1422 out of the aperture 1441 in the top of the mold. Alternatively, the plunger 1415 may be advanced manually. As illustrated in FIG. 14C, a pin 1455 is inserted into the aperture 1441 in the mold base 1440 to seal the aperture, and the entire apparatus is flipped upside down. The suppository material, e.g., liquid medication 52, is then allowed to cure. Thereafter, the suppository 1405 and device 1402 combination can be de-molded and packaged.

For devices that include a hollow plunger that is open at both ends, one can use a solid rod in the mold. The mold actions, i.e., movements of the solid rod, for moving the gas out through the aperture in the mold can be the same as those described for the plunger 1415 shown in FIG. 14B. After the suppository has been allowed to cure, the solid mold rod can be removed and the hollow plunger inserted into the barrel containing the suppository. Example mold actions of a solid rod that moves into and out of a mold during the manufacturing of a suppository are illustrated FIGS. 19A-19K, and are described elsewhere herein.

Figure 15C:
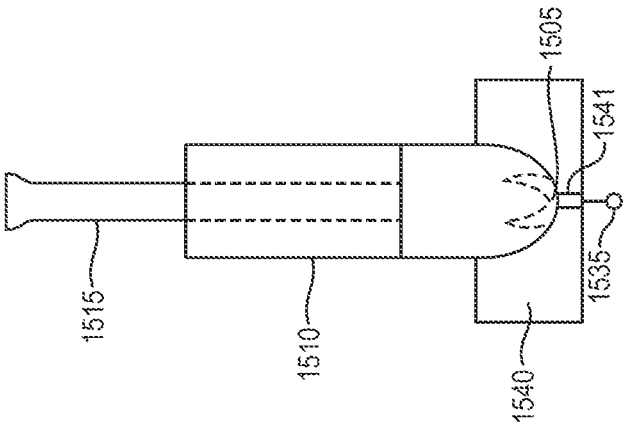
FIGS. 15A-15C are diagrams illustrating embodiments of a process of manufacturing a suppository from a front end of a barrel having fins.
Figure 15B:
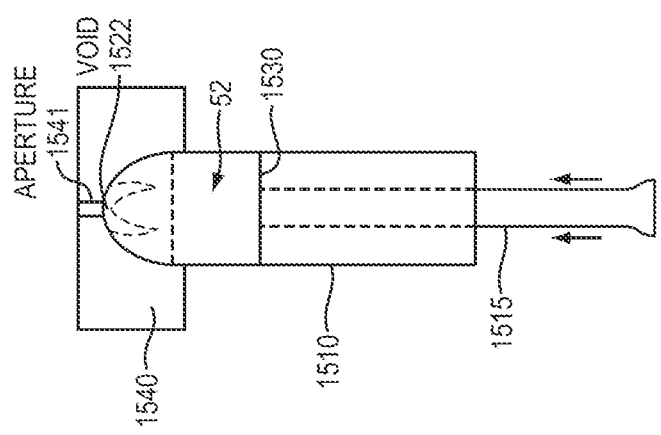
Figure 15A:
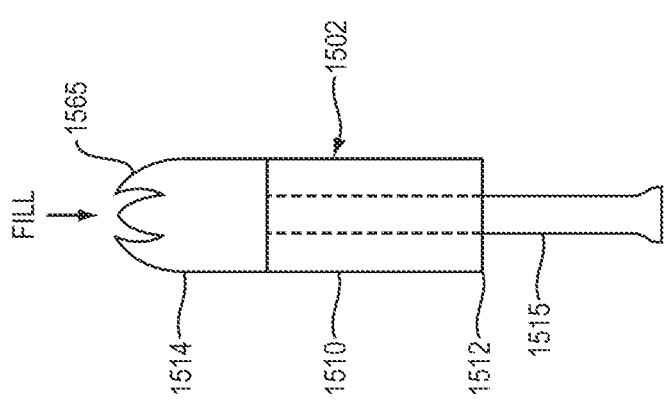

FIGS. 15A-15C are diagrams illustrating an embodiment of a process of manufacturing a suppository from a front end of a barrel 1510 having fins 1565.

As shown in FIG. 15A, a device 1502, including a barrel 1510 preassembled with a plunger 1515, is held upright during an initial phase of the manufacturing process. The plunger 1515 can be solid or formed with a platform base 1560 (FIG. 15B), as shown. The plunger 1515 is kept at a level low enough to allow for the proper dose of a substance, e.g., liquid medication to be filled into the forward end (insertion end) 1514 of the barrel 1510. After the liquid medication has been poured or otherwise filled into the barrel 1510, a mold 1540 having a rounded or bullet shaped tip end 1543 is positioned over, and is optionally coupled to or attached to, the top forward end (insertion end) 1514 of the barrel as illustrated in FIG. 15B. Alternatively, or in addition, the filled unit (barrel 1510) can be placed up into the mold 1540 via a manual or automated process. The mold 1540 has an aperture 1541 that allows the escape of air or other gas from the void 1522 between the level of the liquid medication 52 and the inner side of the top of the mold 1540. A mold action (or alternatively, applied manual force) at the end of the plunger 1515 advances the solid plunger, or plunger with platform 1560, up (indicated by arrows in FIG. 15B), to push the liquid 52 into the mold 1540 and any gas (e.g., air) within the void 1522 out of the aperture 1541 in the top of the mold. As illustrated in FIG. 15C, a pin 1555 is inserted into the aperture 1541 in the mold base 1540 to seal the aperture, and the entire apparatus is flipped upside down. The suppository material, e.g., liquid medication 52, is then allowed to cure. Thereafter, the suppository 1505 and device 1502 combination can be de-molded and packaged.

The suppository 1505 is manufactured in contact with or around the fins 1565 of the barrel 1510, which helps to secure the suppository in the barrel during packaging, shipping and subsequent administration by a user.

Described herein are molds that shape the tip of the suppository. Such molds may be made from, for example, steel, wood, plastic, silicone, or any combination of materials. The molds may be firm or pliable, thick or thin, allowing for the shaping of the end of the suppository. Rather than through a mold, a secondary process, such as thermal melting, could be used to shape the tip of the suppository.

FIGS. 16A-16C are diagrams of example molds that can be used to shape the tip of the suppository during manufacturing including curing. In the embodiment shown in FIGS. 16A-16B, mold 1640a includes a mold tip that is made of a thin silicone membrane 1640b which, after curing, allows for ease of de-molding by pushing on the silicone membrane 1640b to release the suppository and device combination. Alternatively, the mold may become a part of the packaging after curing.

As shown in FIG. 16C, multiple units can be filled with the use of a mold rack 1670. The mold rack 1670 supports the mold 1640c for molding multiple units of suppositories 1605. As shown, the mold 1640c is placed on top of the mold rack 1670, with the mold rack including cut-outs or cavities 1671 for receiving the portions of the mold 1640c that shape the tip of the suppository. After curing, the units can be separated at separation line 1675. The filled unit, along with the mold acting as a protective cap, can then be packaged.

Figure 17B:
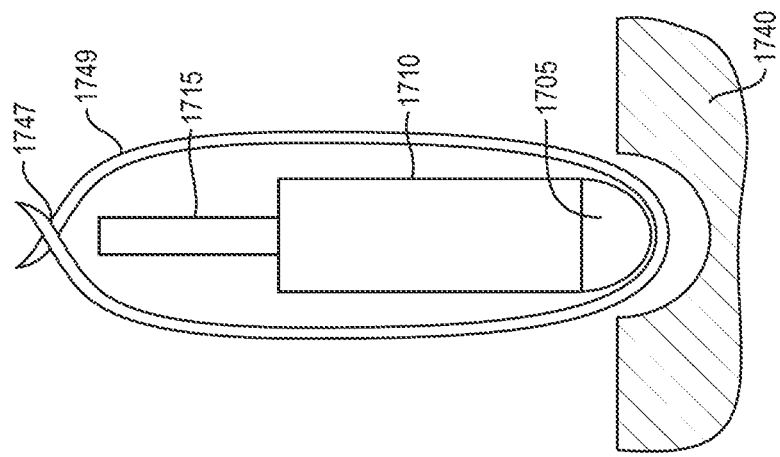
FIGS. 17A-17B and 18A-18B are diagrams of example mold liners that can be used to wrap the prefilled suppository and device unit after manufacturing the suppository and allowing it to cure.
Figure 17A:
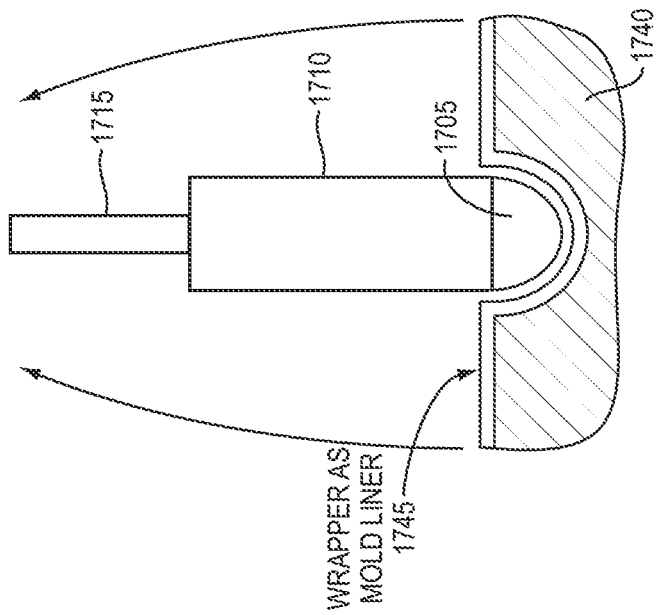
Figure 18B:
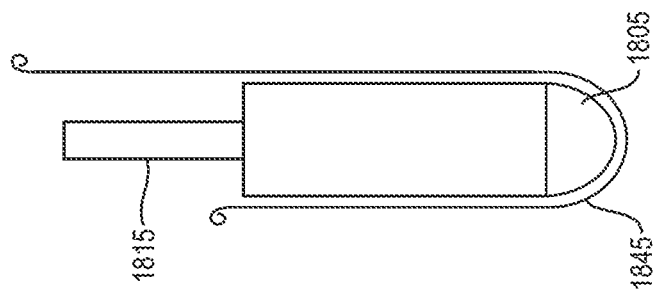
Figure 18A:
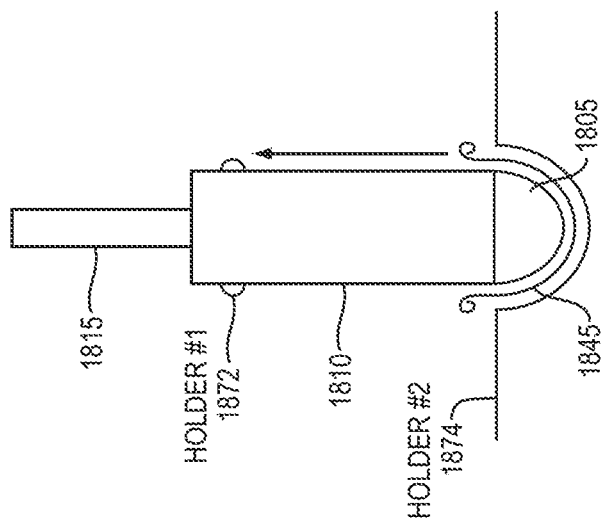

FIGS. 17A-18B are diagrams of example mold liners that can be used to wrap a prefilled suppository and device unit after manufacturing and curing. A mold 1740 may have a liner 1745 that allows the entire manufactured unit (i.e., suppository 1705, barrel 1710 any plunger 1715) to be wrapped in the liner of the mold after the curing of the suppository medication as shown in FIGS. 17A-17B. As shown in FIG. 17B, the mold liner 1745 is wrapper that is sealed at the top 1747 and sides 1749, thus forming a packaging for the unit. The wrapping 1745 can be a liner to a mold, as shown, or it can be the mold itself. In one embodiment, the mold liner 1745 may be a sleeve that the entire unit fits into. The mold liner holds the shape of the tip of the suppository and folds up to seal the entire unit. The individual unit can be opened with the use of a pull tab, by separation of a two-part package with multiple tabs, by unwinding of a bound package, or by other suitable means for opening a sealed packed as is known in the art. FIGS. 18A and 18B illustrate a wrapper 1845 that is a fitted sock fitting snug at the end of the barrel 1810. The wrapper 1845 can be a mold or a mold liner. As shown in FIG. 18A, the device (i.e., suppository 1805, barrel 1810, and plunger 1815), including the wrapper 1845, can be held upright by a holder anywhere along the device until curing is complete. Two example holders and example positions for holding the device are illustrated as holder 1872 and holder 1874 in FIG. 18A. After curing, the wrapper 1845 is unrolled upward, as illustrated in FIG. 18B, and sealed at the top.

Figure 19B:
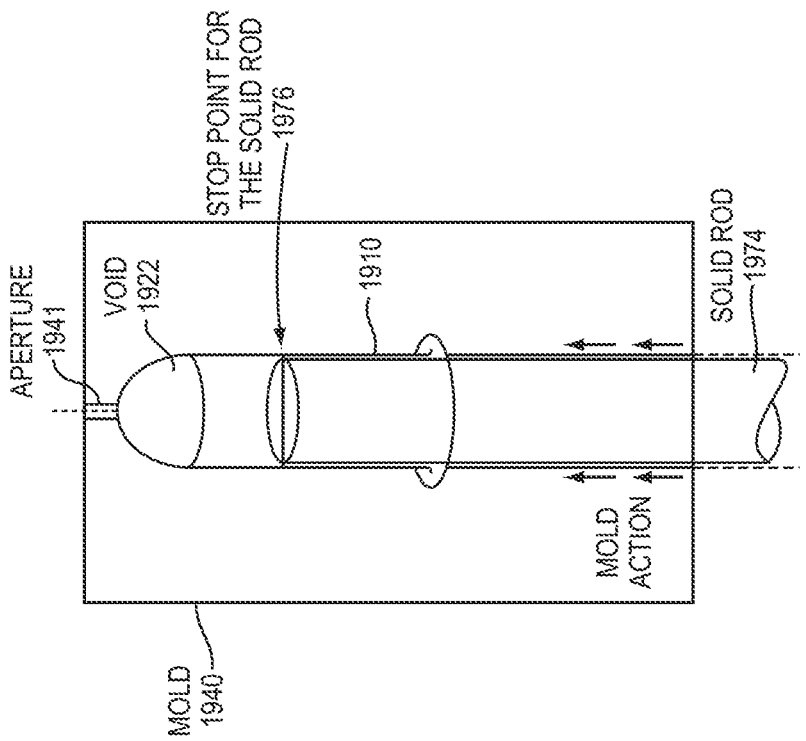

FIGS. 19A-19H are diagrams illustrating an apparatus and process for manufacturing a suppository using a multiple action, convertible mold. The figures show the steps of manufacturing the suppository and the elements and actions of a multiple action, convertible mold. FIGS. 19I-19K are diagrams illustrating alternative elements and steps of the apparatus and process of FIGS. 19F-19H. Thus, two options for curing and de-molding are illustrated, with the elements and steps illustrated in FIGS. 19A-19E being the same in the manufacturing process for both options.

Figure 19A:
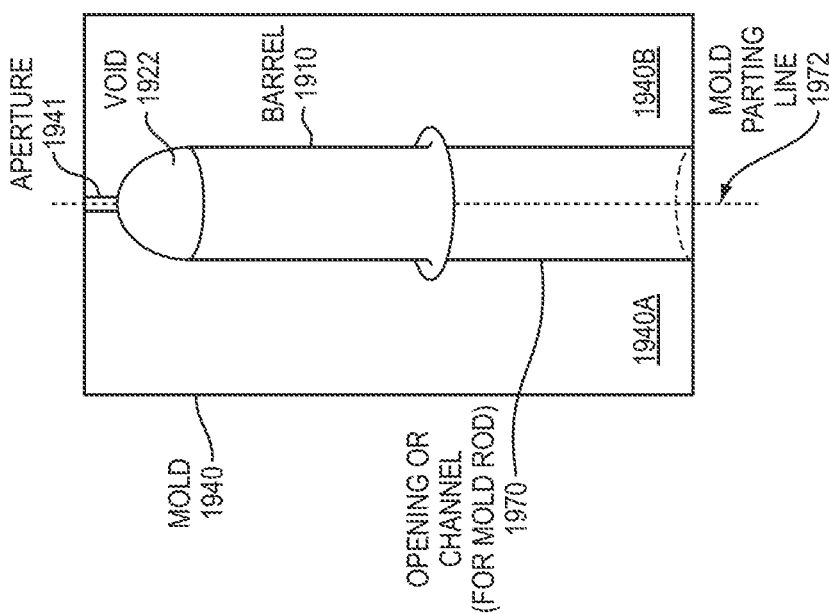
Figure 19D:
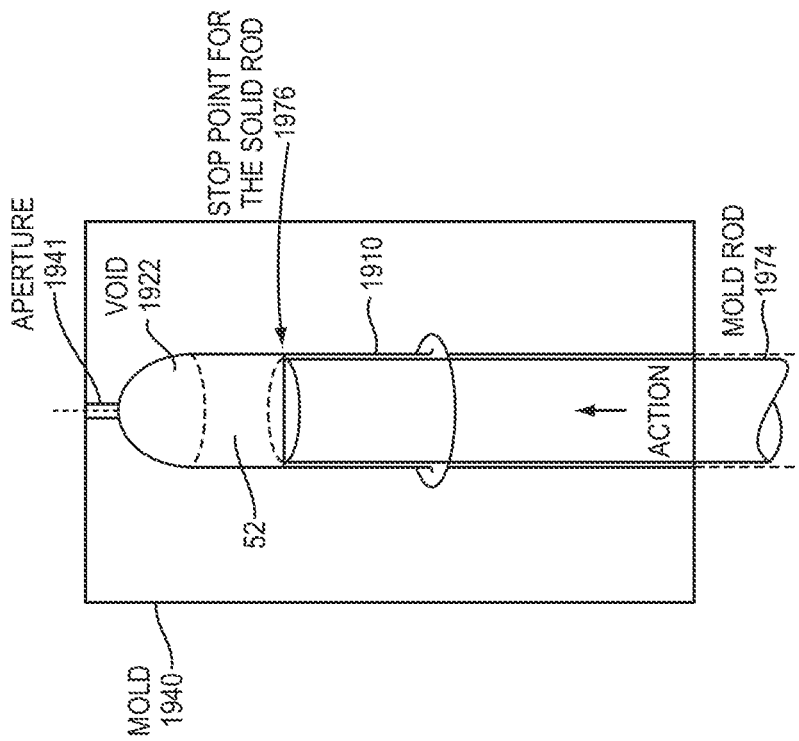

As shown in FIG. 19A, a mold 1940 includes two parts 1940A and 1940B. The mold 1940 can part open at parting line 1972 for insertion of a device element, e.g., barrel 1910. Parting of mold 1940 is one mold action of the multi-part mold. FIG. 19A shows the barrel 1910 positioned inside the mold 1940. Also shown is a void 1922 between the barrel 1910 and the mold 1940. The void 1922 is in fluid communication with an aperture 1941 in the mold 1940, which allows for filling of the void with suppository material through the aperture. An opening or channel 1970 is provided in mold 1940 to receive a mold rod 1974 of the multi-part mold, as shown in FIG. 19B. The mold rod 1974 can be a solid rod member. In one mold action, the solid rod rises up through opening 1970 and into the barrel 1910 until the rod reaches stop point 1976. The mold rod 1974 can be configured to completely fill the cross-sectional area of the barrel 1910. In this way, the mold rod 1910 can prevent the suppository material, e.g., liquid medicine, from leaking out past the rod during filling of the mold 1940 with suppository material and subsequent manufacturing processes.

Figure 19C:
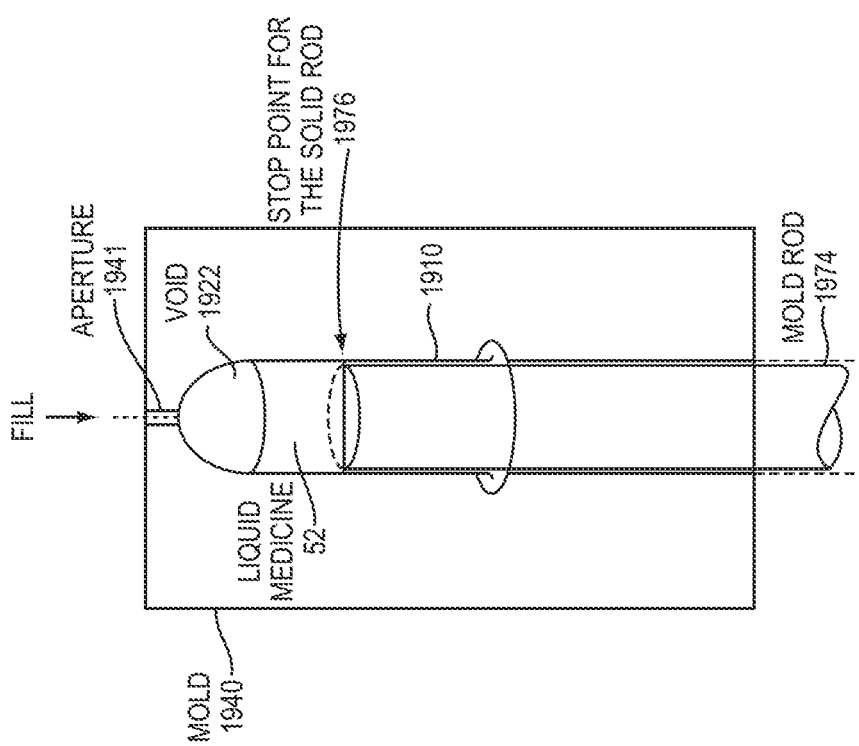
Figure 19F:
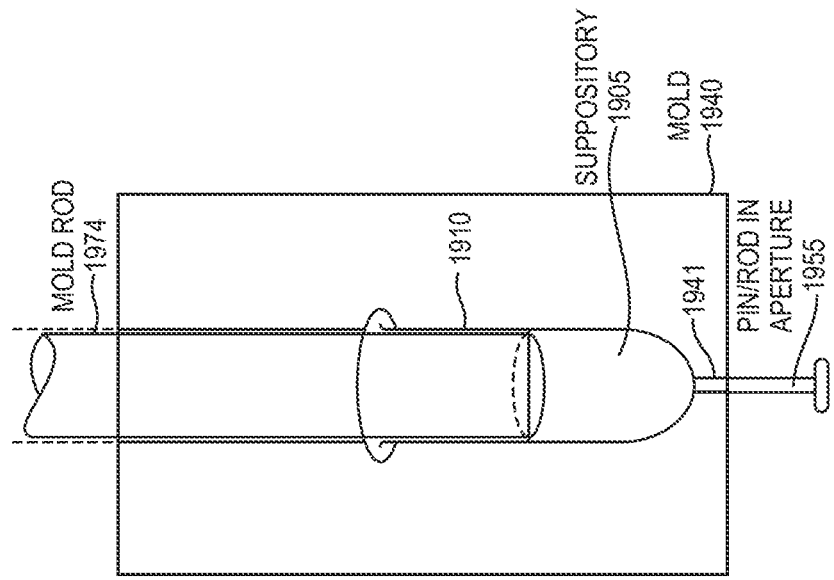

As shown in FIG. 19C, once the mold rod 1974 is in place, suppository material 52, e.g., liquid medicine, is filled through aperture 1941 and void 1922 into the barrel 1910.

As illustrated in FIG. 19D, another mold action moves the mold rod 1974 up toward the aperture 1941, thereby moving the substance 52 into the void 1972 and displacing any gas present. As the rod 1974 moves up, the gas can escape through aperture 1941.

Figure 19E:
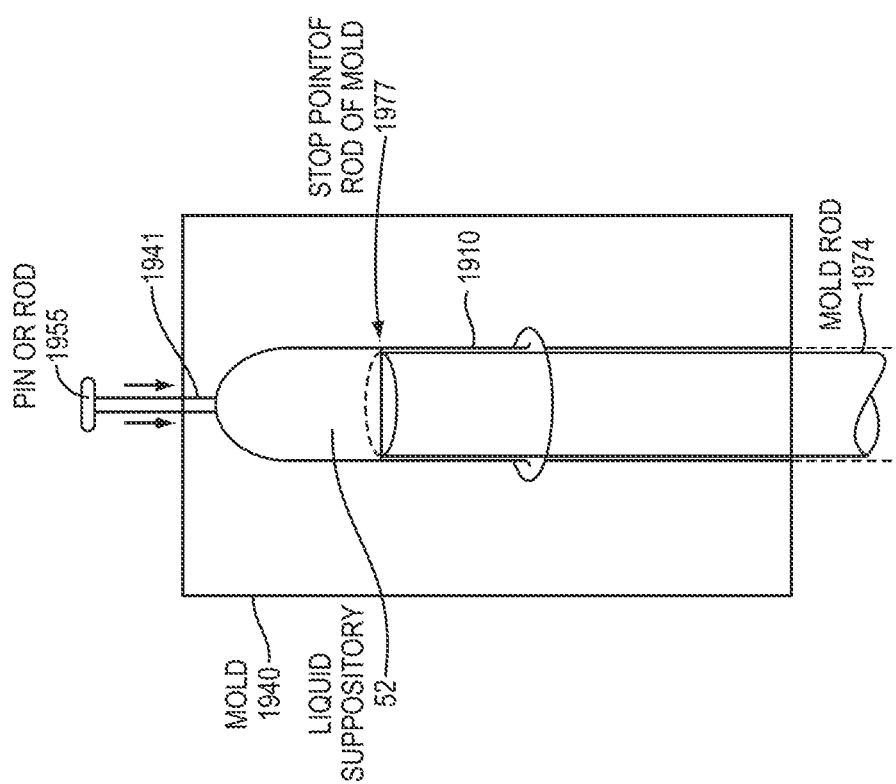
Figure 19J:
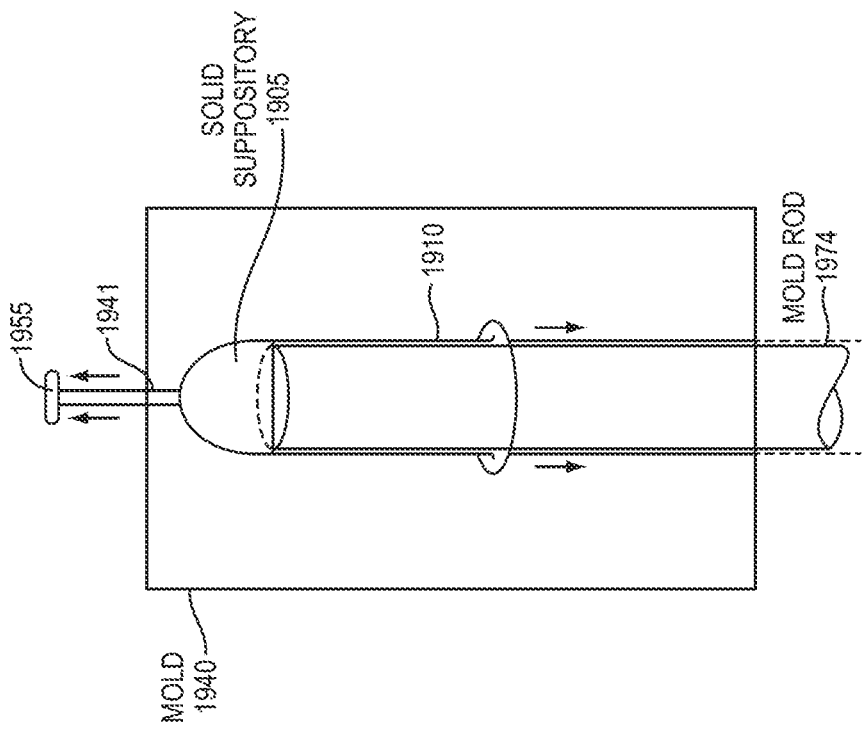
FIGS. 19I-19K are diagrams illustrating alternative elements and steps in the apparatus and process of FIGS. 19A-19H.
Figure 19I:
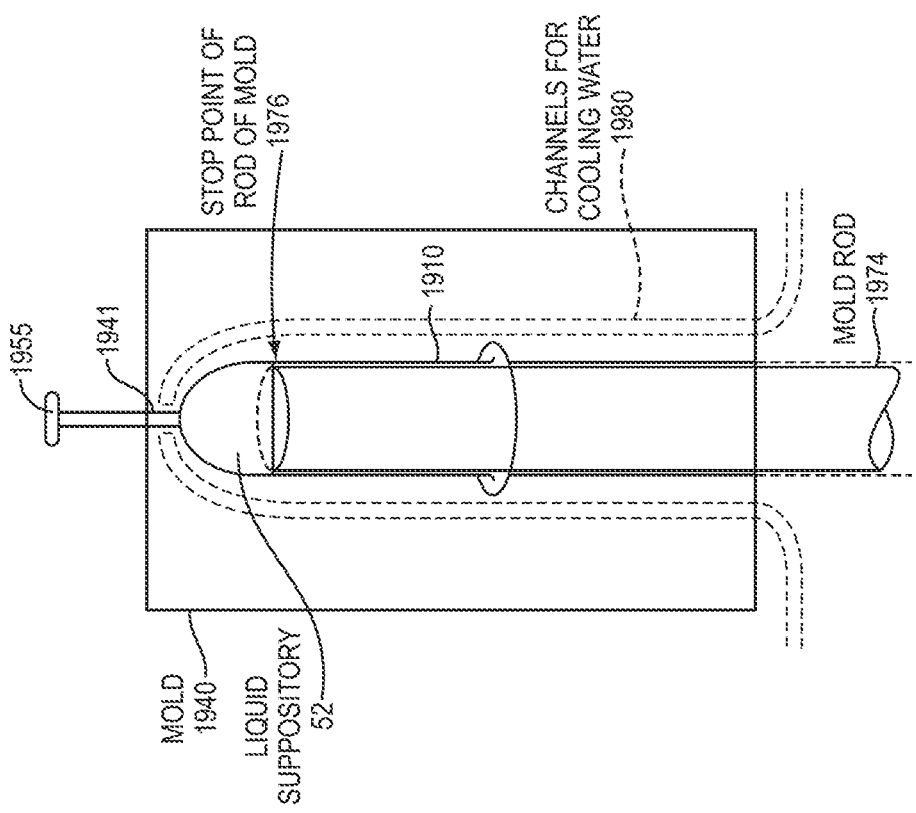
Figure 19K:
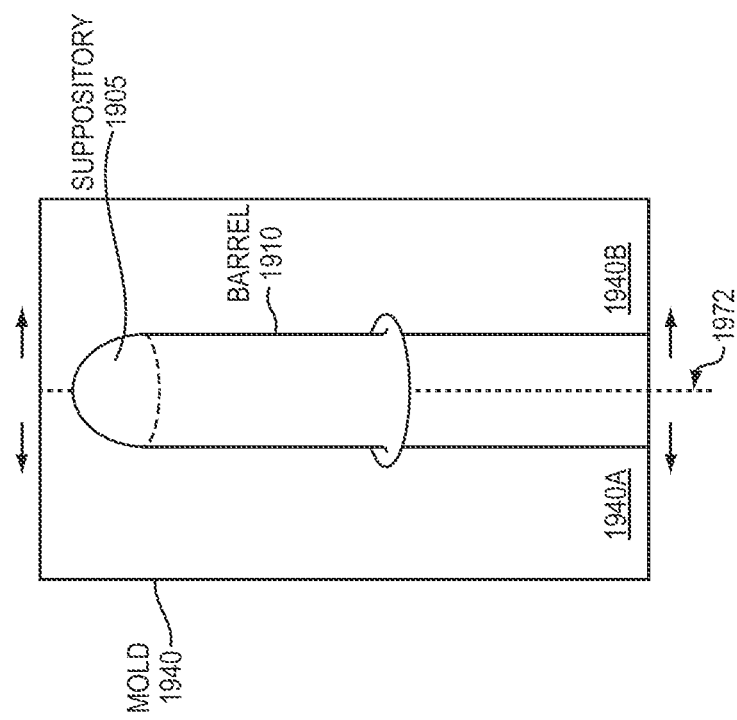

FIG. 19E shows the mold rod 1974 after having moved up toward the aperture 1941 and past stop point 1976 of FIG. 19D to stop point 1977. In another mold action, a pin 1955 is inserted into the aperture 1941. Alternatively, another rod member is moved down into the aperture 1941.

In one option (Option A), illustrated in FIGS. 19F-19H, the process for manufacturing the suppository includes flipping the mold 1940 before allowing the suppository material 52 to cure. By flipping the mold in Option A, as shown in FIG. 19F, the suppository material 52 can settle with gravity forming suppository 1905 and, therefore, the cycle time can be reduced. As shown in FIG. 19G, the pin 1955 (or rod) is removed from aperture 1941 and the mold rod 1974 is retracted from the mold 1940, which can be accomplished by one or more mold actions. FIG. 19H illustrates parting of the mold 1940 along parting line 1972 into parts 1940A and 1940B, which can be accomplished by a mold action. The combination of suppository 1905 and device (i.e., barrel 1910) can be ejected from the mold 1940 via the parting mold action.

In another option (Option B), illustrated in FIGS. 19I-19K, the process includes injection of a cooling fluid to solidify the suppository liquid medication without flipping the mold 1940. That option may be particularly suited for use in an automated process. Cooling can also be used in Option A to further reduce cycle time. As shown in FIG. 19I, cooling fluid (e.g., cold water) is circulated through channels 1980 in mold 1940. The cooling can speed the curing process of the suppository material. After the circulation of cooling fluid is stopped, the pin 1955 (or rod) is removed from the aperture 1941 and the mold rod 1940 is retraced from the barrel 1910 and out of the mold 1940, as shown in FIG. 19J. Next, as shown in FIG. 19K, the mold 1940 separates along parting line 1972 and ejects the suppository 1905 and device (barrel 1910) combination.

Mold actions or movements of a mold rod 1974 of a multiple action mold are shown in FIGS. 19A-19K and have been described in reference to mold 1940. The same or similar mold may be convertible to allow similar mold actions with a plunger that has a platform, such as the plunger 1415 shown in FIG. 14A-14C. In the case of a plunger with a platform, the mold actions can convert to using the plunger instead of the solid rod that is shown in FIGS. 19A-19K. The advantage of a convertible, multi-action mold is that any suppository can be manufactured within the barrel with any plunger, including those described herein. A manufacturing system that includes a convertible mold may be configured to allow forming suppositories of multiple sizes and to accommodate plungers of varied designs. If, for a particular product, a plunger with a platform is desired, the system can fill the suppository material, e.g., liquid drug, into the insertion device just as for a solid or hollow plunger. The ability to accommodate plungers of different designs can reduce the cost of manufacturing the suppositories.

Although embodiments are shown with a convertible mold positioned vertically, the mold may be positioned sideways. A sideways mold may also include an aperture in the mold to allow air or gas to escape the void in the mold during or after the filling of the mold with the suppository material. It may be useful to position the mold sideways to be able to utilize gravity in the parting of the mold, the insertion of a blank barrel, and the ejection of the finished product.

FIGS. 20A-20D illustrate example processes for manufacturing a suppository without using a mold or a wrapper. As shown in FIG. 20A, an element 2002 includes a barrel 2010 and a plunger 2015 positioned in the barrel. As shown, the plunger 2015 includes a platform 2046. A mechanical seal is established between the platform 2046 and the inside of the barrel 2010. Alternatively, a seal can be established via pins or slides, as for example described in references to FIGS. 12C-12D.

As shown in FIG. 20B, a solid or semi-solid suppository substance 50 is applied into element 2002 using an application nozzle 2080. The nozzle 2080 is initially positioned at or within element 2002 and injects the substance 50 while withdrawing from the element 2002. Withdrawing the nozzle at a constant rate and using an appropriately shaped nozzle, one can create a suppository 2005a with a straight domed shape, as shown in FIG. 20B. Withdrawing the nozzle 2080 with intermittent pausing can created a suppository 2005b with a scalloped shape, as shown in FIG. 20C. Twisting the nozzle 2080 during withdrawal can created a suppository with a twisted shape, as shown in FIG. 20D. A wrapper (not shown) may be applied to the element and suppository after shaping of the suppository.

The efficacy of many drugs administered orally may be reduced or inactivated in the stomach because of acidic and/or enzymatic content of the stomach or because the drug may be subject to digestive attack and/or to microbial degradation. Oral administration of drugs also directs the absorbed substances through the metabolism process, including the liver and the kidneys, where the drugs' effectiveness can be further reduced or inactivated. Drug dosages are carefully scrutinized for absorption rates in order to prevent overburdening the liver and kidney organs. Non-steroidal anti-inflammatory drugs can cause severe digestive distress when administered orally. For these reasons, rectal medication is often a more effective mode of delivery for the administration of a variety of drugs for various medical conditions.

Rectal suppositories are composed of active pharmacological ingredients and inactive binding agents that maintain the drug in a desired shape and stable form prior to, and during, insertion into the rectum. The inactive binding agents are designed so that the suppositories remain stable at or below room temperature. Depending on the binding agent used, the suppository is designed to melt or dissolve at, or above, body temperature or by absorbing water, so that the active pharmacological ingredient can be released for absorption by the mucosa lining of the rectum. Rectal suppositories are formed to ease insertion and are commonly manufactured to maintain a torpedo or bullet shape appearance.

Rectal suppositories employ medications that offer topical and/or systemic therapeutic effects. The active ingredient in rectal suppositories is often intended to be directly absorbed in by the rectal venous plexus to be distributed throughout the body by the blood circulation bypassing the portal vein and the liver. Therefore, a rectally applicable medicament form is preferable, particularly for the drugs for which the effective ingredient causes stomach disorder with oral administration or the ingredient is susceptible to decomposition in the digestive tract or liver, resulting in a decreased effectiveness of the medication.

The effectiveness and benefit of rectal suppositories can be improved with proper positioning within the rectum, above the anorectal line (i.e., above the dentate line dividing the anal canal and the rectum). For example, rectal suppositories used for the treatment of internal hemorrhoids may be best able to treat the origin of the inflammation if the suppository is placed in the lower rectum, just above the anorectal line. On the other hand, rectal suppositories used to treat digestive diseases, such as ulcerative proctitis or distal colitis, may be better positioned higher in the rectum at a location of the farthest site of disease origin.

FIGS. 1A and 1B of U.S. application Ser. No. 12/287,215, filed on Oct. 7, 2008, entitled, "Method And Apparatus For Inserting A Rectal Suppository," the entire teachings of which are incorporated herein by reference, describe the current administration technique in which patients use a finger for insertion of the suppository, along with drawbacks of the technique.

Currently, medication is delivered rectally in a liquid form as a suspension enema, a solid form as a suppository, or a cream, ointment or foam. All of these modes of administration have the disadvantage of leaking from within the body to outside the body quickly after insertion using today's insertion techniques. These modes of administration also cause pain and discomfort in varying degrees. Liquid medications and foam are intended to be retained for at least 3 hours. Because of the bodily impulse to eliminate the contents of the bowel, patients struggle to retain the medicine and are often given sedatives to help relax the body. Rectal suppositories have similar disadvantages, including the time required for the medication to melt before being absorbed by the mucosa lining of the rectum. Finally, creams and ointments, although effective for the topical therapeutic of external tissues and areas affected by prolapsed of internal hemorrhoids, do not reach the treatment area above the anorectal line or the rectum, where hemorrhoids originate and gastrointestinal diseases present themselves.

Proper positioning of rectal medication is important and can have an impact on the efficacy of the treatment. For example, internal hemorrhoids develop in the lower rectum above the anorectal line. Treatment with suspension enemas places the medication above the anorectal line. Treatment with creams and ointments do not reach the anorectal line and only treat the hemorrhoids if they are prolapsed. Suppository medication is the preferred treatment for hemorrhoids, but using the current delivery method, i.e., by using a finger, the medication does not have proper contact with the affected area and, as the suppository melts, it leaks from inside of the body to outside the body. Application of medication within the lower rectum aids in the treatment of hemorrhoids while the medication is in contact with the affected area. Further benefit comes from a drug delivery system that helps the medication stay in the proper position without leaking from inside to outside of the body.

FIG. 21A illustrates an example embodiment of an applicator including a hollow barrel 2110 and a plunger 2115. The barrel 2110 has open proximal 2112 and distal 2114 ends defining a gas flow path 2120, which may be one or more, allowing gas to flow freely through the barrel when the distal end 2114 is positioned in the anal canal and rectum. The proximal end 2112 is defined herein as the end which the plunger 2115 enters, and the distal 2114 end is defined herein as the end past which the plunger pushes the suppository 2105 as it travels toward the rectum.

The barrel 2110 is appropriately sized and shaped to fit within the patient's anal canal and rectum. The plunger 2115 may also be hollow and have open proximal and distal ends defining a gas flow path 2120, allowing gas to flow through the plunger and the barrel. The barrel and plunger are movably coupled together. In some embodiments, the plunger is slightly longer than the barrel. For example, the barrel may be approximately 7½ cm, whereas the plunger may be 8 cm. Other lengths are suitable for administration purposes. Also illustrated is a hollow suppository 2105 with open ends 2107, 2109 defining the gas flow path 2190, thereby allowing gas to flow through the suppository 2105, the plunger 2115, and the barrel 2110 while the suppository is loaded in the applicator and the plunger is movably coupled with the barrel.

FIG. 21B illustrates a cross section of the suppository 2105 with its gas flow path (open space 2192) through the medicament combination 2194 of base and active ingredient. It should be understood that a single gas flow path may be defined by the suppository, including open-structure gas flow paths at the radial edge of the suppository.

Figures 22A, 22B:
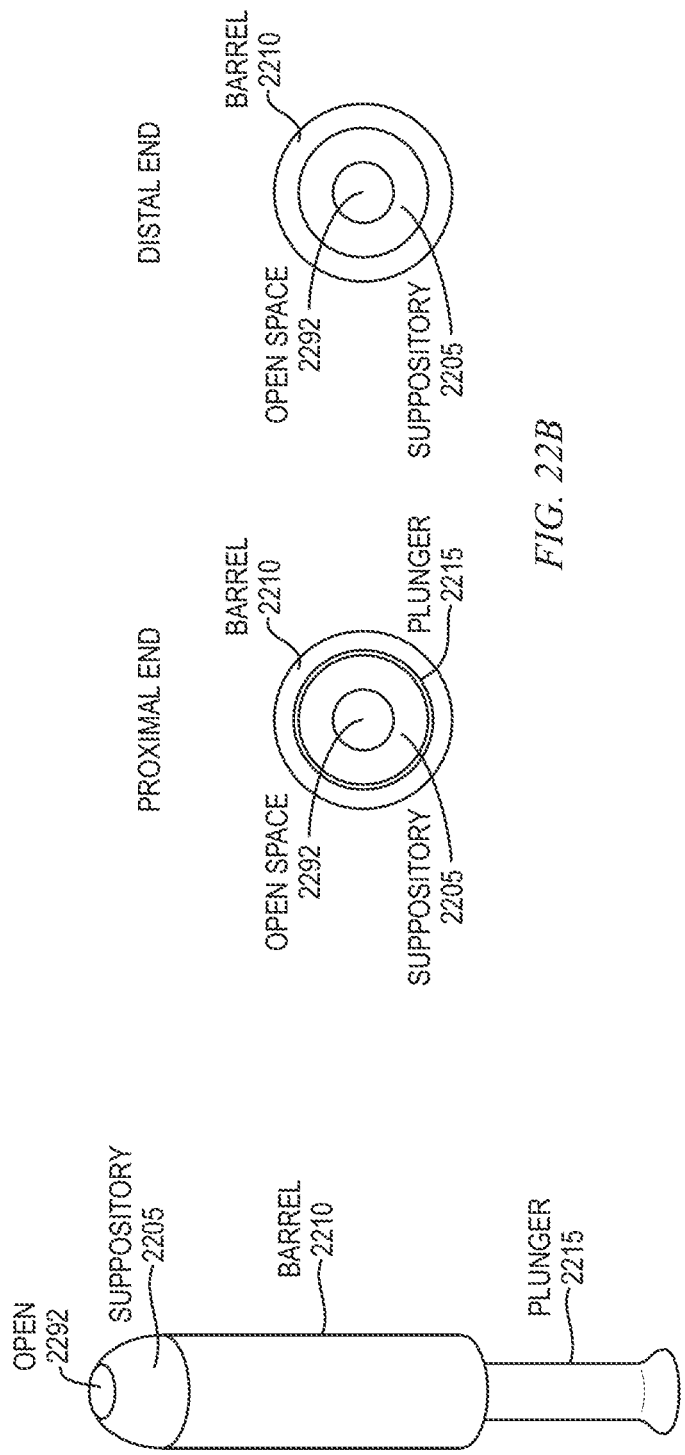
FIG. 22A is a diagram illustrating the barrel, plunger, and suppository in operational arrangement.
FIG. 22B is a diagram of proximal and distal end axial views of the arrangement of FIG. 22A.

FIG. 22A illustrates an applicator configured to insert a suppository 2205 into a human or animal according to an embodiment of the present invention. The applicator may include a barrel 2210 and a plunger 2215 configured to allow gas to flow freely through a gas flow path of the applicator during the administration placement of the suppository 2205 past the anus into the rectum and during withdrawal of the device from the rectum and anus.

The gas flow path may be a single gas flow path or multiple gas flow paths. The suppository may be loaded in the proximal end or distal end of the applicator, depending on an internal structure of the barrel 2210, plunger 2215, or combination thereof. The suppository 2205 further allows gas to flow freely through the gas flow path, illustrated as open space 2292, during administration, where the gas flow path of the suppository and plunger are arrangeable to be aligned.

FIG. 22B illustrates the cross section of the assembled applicator (i.e., barrel 2210 and plunger 2115) with the suppository 2205 from distal and proximal ends perspectives. The gas flow path, illustrated by open space 2292, is maintained through the apparatus and the suppository 2205 from both ends, thereby allowing gas to flow freely during the administration placement of the suppository 2205 past the anus into the rectum and during withdrawal of the device from the rectum and anus.

FIGS. 23A-23D illustrate another example embodiment of an applicator including a plunger that continues to maintain the gas flow path(s). Numerous other plunger configurations are envisioned where the gas flow path is maintained within the applicator and suppository during use.

FIG. 23A illustrates an example embodiment of an applicator including a hollow barrel 2310 and a plunger 2315. The barrel 2310 has open proximal 2312 and distal 2314 ends defining a gas flow path 2320, which may be one or more, allowing gas to flow freely through the barrel when the distal end 2314 is positioned in the anal canal and rectum. The barrel 2310 is similar to barrel 2110 described in reference to FIG. 21A. The plunger 2315 has fins 2320 configured to maintain gas flow path(s) 2120 when the plunger is inserted into the barrel 2310, allowing gas to flow between the plunger 2315 and the barrel 2310. The barrel 2310 and plunger 2315 are movably coupled together. The plunger 2315 can be slightly longer than the barrel 2310. For example, the barrel may be approximately 7½ cm, whereas the plunger may be 8 cm. Other lengths are suitable for administration purposes.

Also illustrated in FIG. 23A is a hollow suppository 2305 with open ends 2307, 2309 defining a gas flow path 2390, thereby allowing gas to flow through the suppository 2305 and through one or more flow paths, e.g., gas flow paths defined by the plunger 2315 and the barrel 2310, while the suppository is loaded in the applicator and the plunger is movably coupled with the barrel.

FIG. 23B illustrates a cross section of the plunger 2315 having fins 2330. FIG. 23C illustrates a cross section of the plunger 2315 positioned within the barrel 2310, including open spaces 2320 (gas flow paths) defined between the fins 2330 of the plunger 2315 and an inside of the barrel 2310. FIG. 23D illustrates a cross section of the plunger 2315 within barrel 2310 with suppository 2305 loaded into the device. Open spaces 2320 (gas flow paths) defined between the fins 2330 of the plunger 2315 and an inside of the barrel 2310 are in fluid communication with a gas flow 2390 path defined through the suppository 2305.

Examples of other embodiments are described in U.S. application Ser. No. 12/287,215, the entire teachings of which are incorporated herein by reference. Further, a description of proper placement of the suppository inside the body is presented therein and incorporated herein by reference.

Figure 24A:
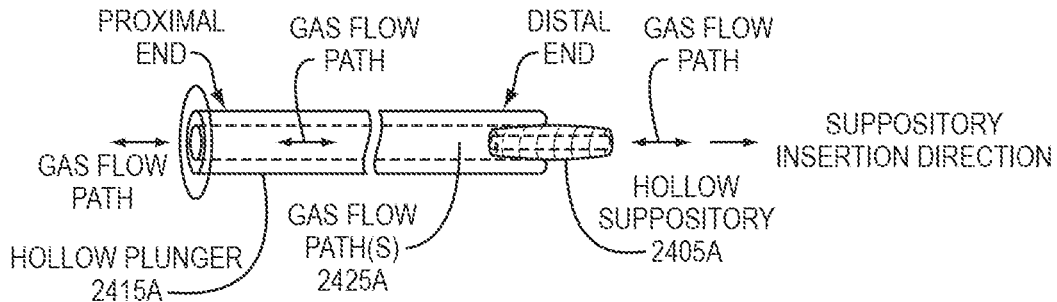
FIG. 24A is a diagram of a suppository insertion device having a plunger and no barrel.

In an alternative embodiment, as illustrated in FIG. 24A, a single element, referred to herein as a plunger 2415*a*, defines a gas flow path 2425*a*. The gas flow path 2425*a* is configured to allow gas to flow from the rectum to outside the body while a distal end of the plunger 2415*a* is within the rectum and, using the same configuration, maintains the gas flow path 2425*a* until the plunger is withdrawn fully outside the body. In an embodiment in which the plunger is used in conjunction with a suppository that defines a gas flow path, the gas flow path of the plunger is aligned with the gas flow path of the suppository during application of the suppository into the rectum.

It should be understood that the shape of the suppository illustrated in FIG. 24A with a gas flow path associated therewith can be produced using molding techniques described herein or the gas flow path(s) can be formed (e.g., bored or, for example, melted with a thin rod (not shown) after a suppository has been solidified without a gas flow path.

Figures 1, 24B:
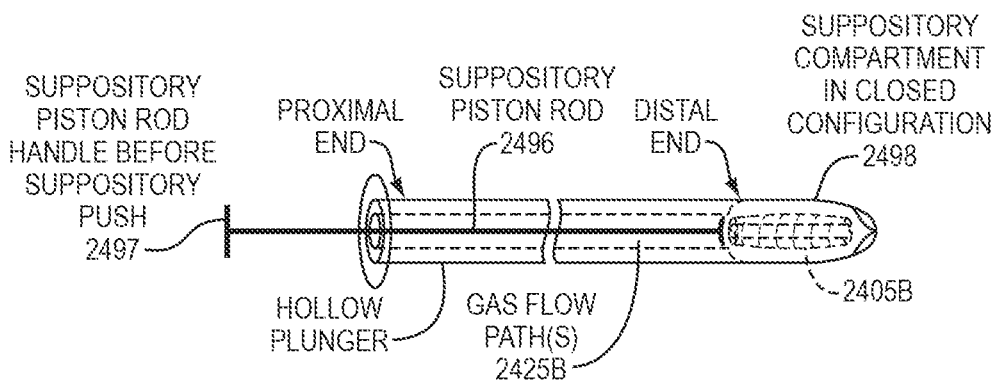
Figures 2, 24B:
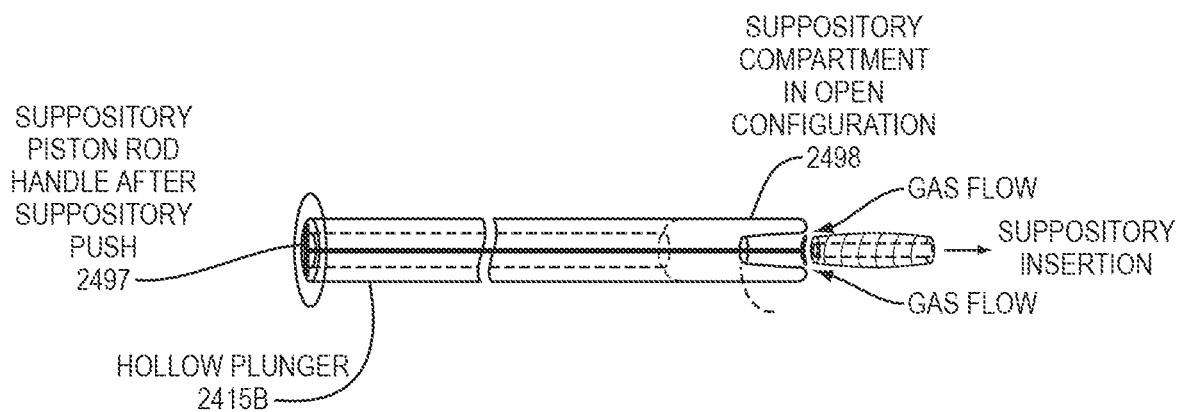

A mechanism (not shown), such as a piston rod as illustrated in FIGS. 24B-1 and 24B-2 and described below, may be employed to push the suppository 2405*a* from the plunger 2415*a* into position once the distal end of the plunger is within the rectum. The piston rod may be configured to maintain the gas flow path of the plunger throughout or for portions of the insertion and withdrawal processes such that the suppository is appropriately positioned within the rectum by the patient or person performing the application task.

Alternatively, as illustrated in FIGS. 24B-1 and 24B-2, the suppository 2405*b* need not define a gas flow path, and the plunger 2415*b* of the single element apparatus need simply facilitate a gas flow path during and after the suppository is positioned within the rectum. In one example embodiment, the plunger 2415*b* includes a piston rod 2496 that can push the suppository 2405*b* from within a suppository compartment 2498, at a distal end of the plunger, past an end of the compartment and into the rectum. FIG. 24B-1 illustrates the position of piston rod 2496, including piston rod handle 2497, relative to plunger 2415b before the suppository push. FIG. 24B-2 illustrates the position of piston rod 2496, including piston rod handle 2497, after the suppository push. The gas flow path(s) 2425b are maintained from insertion of the suppository into the rectum until withdrawal of the plunger from the anus to ensure suction does not displace the suppository from its resting position in the rectum following insertion.

It should be understood that holes or gaps may be provided in a wall of the compartment 2498 to allow air and gas to enter the compartment and gaseously connected gas flow path, thereby minimizing or eliminating air or gas from being pushed into the rectum to prevent discomfort from inserted gas or expulsion of the suppository shortly after insertion because of inserted gas. The holes or gaps are configured (e.g., sized and shaped) such that little to no effects on sensitive tissue during the insertion and withdrawal processes are experienced by the patient. For example, many small holes can be employed to provide a substantially smooth surface rather than large apertures.

Alternatively, the piston rod 2496 or other element(s) (not shown) may be configured to provide suction of gas, but not the suppository, while the distal end of the plunger is within the rectum to withdraw inserted gas so as to reduce discomfort caused from inserted gas or expulsion and reduce likelihood the suppository will be expelled shortly after insertion because of the inserted gas.

Certain diseases are treated by way of a suppository containing a drug. Current suppositories have "torpedo" configurations, and, therefore, can be difficult to insert into a rectum or, even if inserted, may be dislodged due to insertion of air into the rectum during the insertion process. An embodiment of the present invention configures the suppository to have at least one gas flow path. Another embodiment includes a suppository with gas flow path and suppository insertion device with gas flow path configured to align with the suppository gas flow path. Through use of the suppository insertion device, the suppository can be properly inserted into the rectum with comfortable and effective results for a patient.

It should be understood that the example embodiments disclosed herein for the manufacturing of suppositories can be applied to the manufacturing of cosmetics, such as lipsticks, lip balms, and deodorants.

For example, in the case of manufacturing lipsticks, all of the foregoing example embodiments apply, meaning that any of the molding, pouring, and assembling techniques can be applied to lipsticks. Other features involved in the manufacturing, tip shaping, and assembly of lipsticks may be more specific to lipsticks than suppositories. Examples of certain features that may be involved in the manufacturing of particular lipsticks are provided below in reference to FIGS. 25A-1 through 30. An example of a customized/personalized ordering system is described in reference to FIG. 31.

FIGS. 25A-1 through 25A-4 illustrate an embodiment of manufacturing lipsticks in which the manufacturing occurs, then a subsequent tip shaping process is applied. In FIG. 25A-1, a substance 2505 is filled into an element 2515 by pouring or other technique in which the substance 2505 extends above the element 2515. In a next step of the process, a mold formed of two halves 2525a, 2525b are directed toward each other to shape the tip of the substance 2505. After the tip is formed 2505', the two halves of the mold 2525a, 2525b are withdrawn from each other and the tip. Subsequently, a wrapper 2530 can be placed over the lipstick 2505' and element 2515. Alternatively, the element 2515 with substance 2505 can be placed into a casing and covered with a casing cover (not shown).

FIG. 25B-1 illustrates an alternative tip shaping process in which a substance in an element according to FIG. 25A-1 can be moved into position to receive a mold 2527 of FIG. 25B-2 that presses downward upon the substance 2505 to form the shaped tip 2505' illustrated in FIG. 25B-3. The final shape of the substance and element of FIG. 25B-4, which is similar to FIG. 25A-4, can then be wrapped in a wrapper 2530 and sent for distribution.

FIG. 26A illustrates an alternative embodiment for forming a lipstick, where a casing sleeve 2615 receives a substance, such as for lipstick, that is held in place above the casing sleeve 2615 by a liner 2610 (optional) until the substance 2605 is set (i.e., solidified), where the substance may be flowed or otherwise positioned within the casing sleeve and thereabove such that the lipstick projects above the casing sleeve for application on a user's lips.

FIG. 26B shows the diagram of the casing sleeve 2615 with the substance 2605 projecting thereabove that is then sent to a tip shaping process, such as the process illustrated in FIGS. 27A-27C.

FIG. 27A is a diagram illustrating a machine that expels a substance with time control to portion out the quantity into and above a casing sleeve 2715. The machine 2720 releases a substance 2705 at an appropriate rate until an appropriate amount of the substance 2705 extends above the casing sleeve 2715. Alternatively, the casing sleeve 2715 may be an extended sleeve or include a liner, and then a portion of the sleeve or the full liner is removed automatically or by hand.

FIG. 27B illustrates an alternative embodiment for shaping a tip of a lipstick (or other substance). A tip shaper 2725 may be a mechanical cutter, heater, drillhead, chipper, or other devices known in the art to form a shape of the lipstick 2705. A difference between the suppositories and, for example, lipsticks is that a selling feature of lipsticks is often a shape and shine of the tip. Therefore, depending on the type of tip shaper 2725 used, a subsequent process, such as flaming, heating, shining or smoothing may be employed.

FIG. 27C includes the substance with molded tip 2705' in its casing sleeve 2715 after the forming and shaping processes are complete.

It should be understood that the casing sleeve may or may not be required, but it does provide for ease of handling should part of the assembly process be manual, such as arranging the casing sleeve with lipstick into a casing. It should also be understood that, in accordance with many of the embodiments disclosed above, the casing sleeve may be in the casing while the lipstick or other substance is flowed into the casing sleeve, thereby reducing hand assembly steps to provide for a fully automated process from beginning to end so that the lipstick is never touched by human hands prior to first use.

Figure 28:
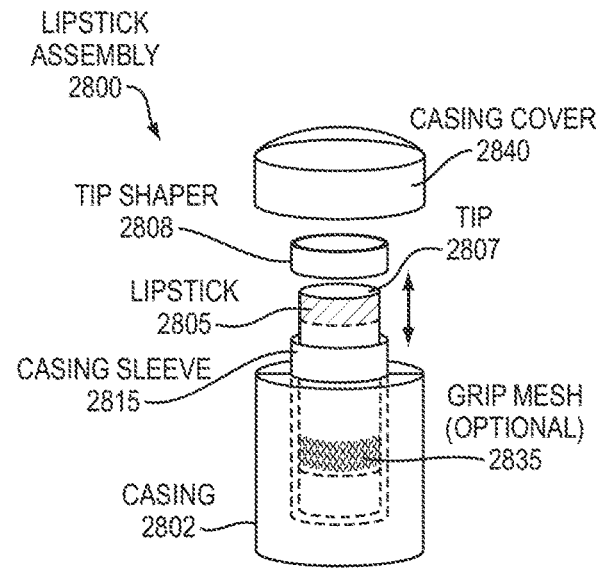
FIG. 28 is a diagram of an example assembly for a lipstick or other cosmetic or sub stance.

FIG. 28 is a diagram illustrating a lipstick assembly 2800 having a casing 2802 in which a lipstick 2805 with a formed tip 2807 is within a casing sleeve 2815 is arranged. The lipstick 2805 may have been manufactured in the presence of a grip mesh 2835 in an optional embodiment. The grip mesh 2835 is any mesh or porous structure with which a semi-solid or solid state of the lipstick 2805 can be integrated. For example, a liquid state of the lipstick 2805 can flow in, around, and below structural elements of the grip mesh, and, after solidification, the solid state of the lipstick 2805 will have a firm connection to the grip mesh 2835.

The grip mesh 2835 within the casing 2802 may be useful in holding the lipstick 2805 within the casing 2802 in a manner that does not require a significant amount of lipstick 2805 to project downward into the casing 2802 while simultaneously ensuring the lipstick 2805 does not fall out of the casing 2802, or casing sleeve 2815 in such embodiments, during application of the lipstick 2805 to a user's lips.

During usage, the grip mesh 2835 may translate upward and downward within the casing 2802 during movement upward and downward of the lipstick 2805 such that the top of the casing sleeve 2815 from the bottom of the casing 2802, or cavity defined therein, is a first distance while the lipstick 2805 is in a most retracted state with respect to a port (i.e., opening) at the top of the casing 2802, and the bottom of the grip mesh 2835 is a second distance from the top of the casing in a most protruding state of the lipstick 2805 through the port, where the first and second distances are approximately the same. Approximately the same in this case means that a differential of the distances is half an inch, quarter of an inch, eighth of an inch, or less. In this embodiment, the lipstick 2805 during the assembly process is formed in an integrated arrangement with the grip mesh such that the lipstick 2805 has a solid connection to the grip mesh 2835, which, subsequently, in the lipstick assembly 2800, enables the user to apply more length of the lipstick 2805 to the user's lips than lipstick assemblies produced without the grip mesh 2835.

The lipstick assembly 2800 may have the lipstick 2805 formed with a tip shaper 2808 during the manufacturing process. The tip shaper 2808 can be used to shape the tip 2807 according to the tip shaper's 2808 shape. The tip shaper 2808 may be heated, for example, or apply any of the other tip-shaping techniques disclosed herein, and applied to an unshaped tip of the lipstick 2805 to melt the tip into its final shape.

The tip shaper 2808 may be discarded prior to assembly of a casing cover 2840 over the casing 2802. Alternatively, the tip shaper 2808 may be kept in position while the casing cover 2840 is coupled to the casing 2802 and, prior to first use, discarded by the user. Still alternatively, the tip shaper 2808 and the casing cover 2840 may be an integrated whole such that the casing cover 2840 shapes the tip 2807 of the lipstick 2805 while being and remaining in coupled arrangement with the casing 2805. It should be understood that the various alternatives with respect to the tip shaper 2808 can be decided based on a given assembly process based on consumer satisfaction of the distributed lipstick product. Moreover, the tip shaper 2808 may be used to provide features in the tip of the lipstick according to categories, as described in reference to FIG. 29 below.

Figure 29:
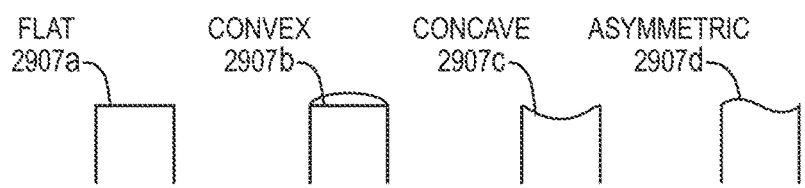
FIG. 29 is a diagram of example categories of tip shapes that may be imposed on a lipstick in accordance with an embodiment of the invention.

FIG. 29 provides examples of categories 2907a-d that can be found in shapes of lipsticks after users have used a lipstick for a shape-defining length of time. Examples of categories include flat 2907a, convex 2907b, concave 2907c, and asymmetric 2907d. Because a lipstick is three-dimensional, the categories may be more complex in shape than the categories illustrated in reference to FIG. 29. For example, there can be another category that includes features of convex and concave at various surface locations across the tip 2807 of the lipstick 2805. The tip shaper 2808 can be provided that can create such three-dimensional complex features across the top of the unshaped lipstick 2705.

Figure 30:
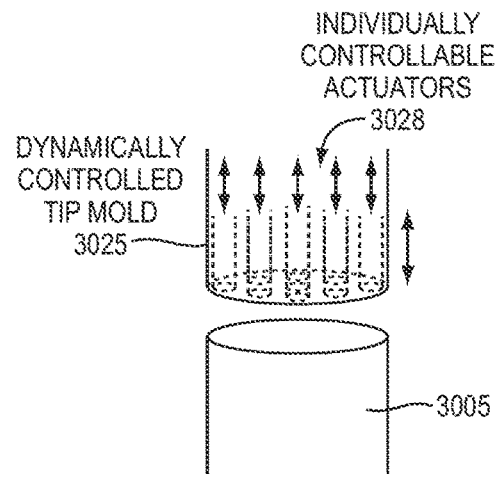
FIG. 30 is a diagram of an embodiment of an automated tip shaper that may shape the tips of a lipstick according to the categories of FIG. 29.

FIG. 30 is a diagram in which a tip shaper 3025 can be a dynamically controlled tip mold that includes individually controllable actuators 3028 that push and pull on an interior surface (i.e., non-contact side) of the dynamically controlled tip mold 3025 to cause a lipstick 3005, or other substance, to have its shape formed in accordance with a selection by a user. Examples of individually controllable actuators 3025 are linear actuators driven by electrical control signals, pneumatic actuators pneumatically driven, and other forms of actuators known in the art that support sufficient motion controlled physical range such that personalized tips of lipsticks can be shaped. It should be understood that the number of individually controllable actuators 3028 define the resolution such that a wide range of shapes can be imparted into the tip of the lipstick. Further, the stiffness of the surface of the dynamically controlled tip mold 3025 must be stiff enough to impress its shape upon the substance forming the lipstick 3005 yet pliable enough to enable the individually controllable actuators 3028 to make sufficient bends in the surface to provide the specific shape.

Figure 31:
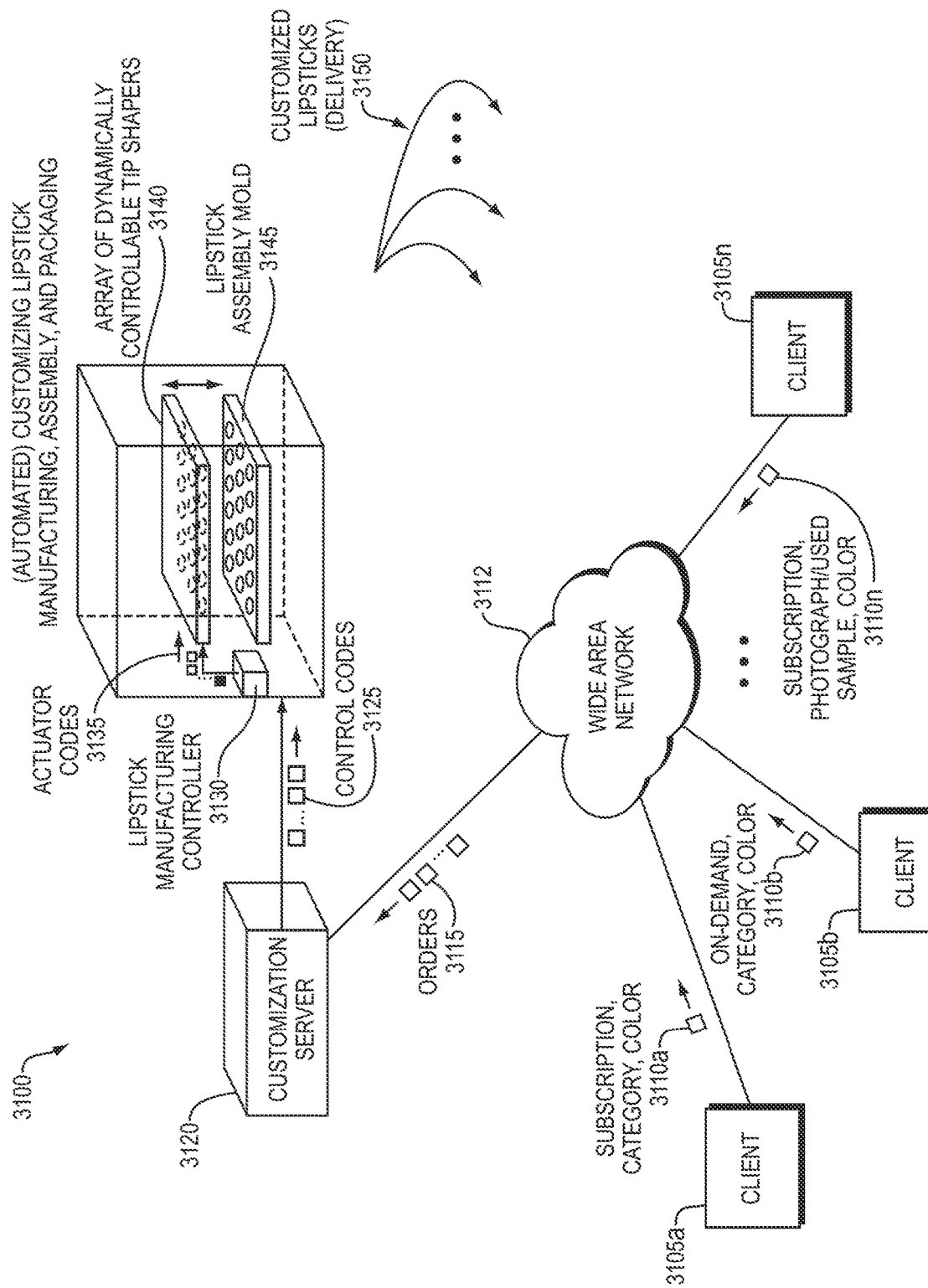
FIG. 31 is a network diagram of a network that may be employed to enable easy ordering of personalized products in accordance with manufacturing of the embodiments disclosed herein.

FIG. 31 is a network diagram 3100 in which clients 3105a-n can submit requests for personalized lipsticks by way of communications 3110a-n. The communications may include indicators corresponding to whether the order is a subscription or on-demand (or other form) order, a category of features representing a shape of a tip of the lipstick, color, and other parameters associated with the personalized lipstick, such as size, and shape of the casing. The communications 3110a-n can be passed through a wide area network 3112, such as the Internet, which are then passed to a customization server 3120 as orders 3115. The customization server 3120 may convert the orders into control codes 3125 that are received by a lipstick manufacturing controller 3130, which may include a tip shaping controller (not shown). The lipstick manufacturing controller 3130 may include a converter module (not shown) that converts the control codes 3125 into actuator codes 3135 that are applied to actuators 3028 (FIG. 30) within an array of dynamically controllable tip shapers 3140. The control codes may also be parsed by the lipstick manufacturing controller 3130 to determine colors of dyes to be applied by the automated machinery to substances used to form the lipstick. The substances are, in this embodiment, flowed into an assembly mold 3145 during manufacturing. Following manufacturing, which may include automated customizing of lipstick forming, tip shaping, casing assembling, and product packaging, the customized/personalized lipsticks 3150 are delivered to the clients 3105a-n.

It should be understood that any form of communications 3110a-3110n can be employed, such as e-mails, text messages, website selections, and so forth, as known in the art. Also, categories of tip shapes can be selected by a user/client by name, selection on a website, or even through photographs, three-dimensional models, or previously-used lipsticks that a user has used, and the customization server 3120 may maintain parameters relating to the personalization within a database (not shown).

As should be understood, any form of computer networking, software, control systems, and other automated processings may be employed that can be used to execute the embodiments disclosed herein. Further, the network of FIG. 31 may also be employed for the ordering of personalized suppository applicators with integrated suppositories in accordance with embodiments disclosed herein. It should be noted that the data flowing between nodes within the network may be modified for the specific personalized device and substance.

In view of the foregoing descriptions of FIGS. 25A-1 through FIG. 31, the following embodiments are now presented:

A $1^{st}$ specific embodiment is a method of manufacturing lipstick, the method comprising: forming a lipstick, the lipstick during forming being in contact with an element configured to hold and protect the lipstick after the lipstick is formed; and shaping a tip of the lipstick.

A 2$^{nd}$ specific embodiment is a method of the 1$^{st}$ specific embodiment wherein the element is a casing sleeve configured to hold and protect the lipstick within a casing after the lipstick is formed.

A 3$^{rd}$ specific embodiment is a method of the 2$^{nd}$ specific embodiment further comprising arranging the casing sleeve within the casing prior to forming the lipstick.

A 4$^{th}$ specific embodiment is a method of the 2$^{nd}$ specific embodiment further comprising arranging the casing sleeve within the casing after forming the lipstick.

A 5$^{th}$ specific embodiment is a method of the 1$^{st}$ specific embodiment wherein shaping the tip is performed during the forming or after the lipstick has been formed but for the shape of the tip.

A 6$^{th}$ specific embodiment is a method of the 5$^{th}$ specific embodiment wherein shaping the tip includes using a tip shaper.

A 7th specific embodiment is a method of the 6$^{th}$ specific embodiment further comprising removing the tip shaper from the lipstick after the lipstick is formed and tip is shaped.

An 8$^{th}$ specific embodiment is a method of the 7$^{th}$ specific embodiment wherein the element is a casing sleeve configured to hold and protect the lipstick within a casing after the lipstick is formed, the method further comprising: arranging the casing sleeve within the casing; and coupling a casing cover to the casing after the lipstick is formed and tip shaper is removed.

A 9$^{th}$ specific embodiment is a method of the 6$^{th}$ specific embodiment wherein the element is a casing sleeve configured to hold and protect the lipstick within a casing after the lipstick is formed, the method further comprising: arranging the casing sleeve within the casing; and coupling a casing cover to the casing over the tip shaper.

A 10$^{th}$ specific embodiment is a method of the 6$^{th}$ specific embodiment wherein the element is a casing sleeve configured to hold and protect the lipstick within a casing after the lipstick is formed, the method further comprising: arranging the casing sleeve within the casing; and maintaining a position of the tip shaper for the tip shaper to serve as a casing cover.

An 11$^{th}$ specific embodiment is a method of the 1$^{st}$ specific embodiment wherein the element is a casing sleeve configured to hold and protect the lipstick within a casing after the lipstick is formed, and wherein forming the lipstick includes forming a casing end of the lipstick opposed from the tip in an integrated arrangement with a grip mesh positioned within or to be positioned within the casing.

A 12$^{th}$ specific embodiment is a method of the 1$^{st}$ specific embodiment wherein forming the lipstick includes projecting a material composing the lipstick through a wall of the element.

A 13$^{th}$ specific embodiment is a method of the 1$^{st}$ specific embodiment wherein the element is a casing sleeve configured to hold and protect the lipstick within a casing after the lipstick is formed, wherein forming the lipstick includes projecting a material composing the lipstick through a wall of the casing sleeve or casing.

A 14$^{th}$ specific embodiment is a method of the 1$^{st}$ specific embodiment wherein the element is a casing sleeve configured to hold and protect the lipstick within a casing after the lipstick is formed, wherein shaping the tip includes using a tip shaper, and wherein forming the lipstick includes projecting a material composing the lipstick through a wall of the casing sleeve, casing, or tip shaper.

A 15$^{th}$ specific embodiment is a method of the 1$^{st}$ specific embodiment wherein forming the lipstick includes using a mold in conjunction with the element.

A 16$^{th}$ specific embodiment is a method of the 15$^{th}$ specific embodiment wherein forming the tip includes using the mold to shape the tip.

A 17$^{th}$ specific embodiment is a method of the 1$^{st}$ specific embodiment wherein shaping the tip of the lipstick includes applying a feature that is within a category of features from among multiple categories of features representing shapes of tips of lipsticks that are created by various users of lipsticks after a shape-defining number of uses.

An 18$^{th}$ specific embodiment is a method of the 1$^{st}$ specific embodiment wherein shaping the tip includes selecting one of multiple tip shapers to apply respective different shapes to the tip of the lipstick.

A 19$^{th}$ specific embodiment is a method of the 1$^{st}$ specific embodiment wherein shaping the tip includes causing a tip shaper to change its shape between shaping the tip of a first lipstick and shaping the tip of a second lipstick.

A 20$^{th}$ specific embodiment is a method of the 1$^{st}$ specific embodiment wherein shaping the tip includes customizing the shape of the tip according to a model selected by a user or according to a sample or image thereof of a lipstick having a shape created in a tip of a previously used lipstick by the user.

A 21$^{st}$ specific embodiment is a method of the 20$^{th}$ specific embodiment further comprising producing the lipstick with customized shape of the tip on a subscription or on-demand basis.

A 22$^{nd}$ specific embodiment is a lipstick with a tip having a feature that is within a category of features from among multiple categories of features representing shapes of tips of lipsticks that are created by various users of lipsticks after a shape-defining number of uses, the lipstick made by the process of: forming the lipstick, the lipstick during forming being in contact with an element configured to hold and protect the lipstick after the lipstick is formed; and shaping a tip of the lipstick to express the feature.

A 23$^{rd}$ specific embodiment is a lipstick of the 22$^{nd}$ specific embodiment wherein the categories of features include flat, convex, concave, and asymmetric features.

A 24$^{th}$ specific embodiment is a lipstick of the 22$^{nd}$ specific embodiment wherein forming the lipstick includes selecting one of multiple tips shapers substantially matching the feature.

A 25$^{th}$ specific embodiment is a lipstick of the 24$^{th}$ specific embodiment wherein shaping the tip includes causing a tip shaper to change its shape in an automated manner between shaping the tip of a first lipstick and shaping the tip of a second lipstick.

A 26$^{th}$ specific embodiment is a lipstick assembly, comprising: an unused lipstick within a casing, the unused lipstick having a tip with a feature that is within a category of features from among multiple categories of features representing shapes of tips of lipsticks that are created by various users of lipsticks after a shape-defining number of uses.

A 27$^{th}$ specific embodiment is a lipstick of the 26$^{th}$ specific embodiment further comprising a grip mesh with which the lipstick opposed from the tip is in integrated arrangement, the grip mesh being positioned within the casing toward the bottom of or below a casing sleeve coupled to the lipstick.

A 28th specific embodiment is a lipstick assembly, comprising: a lipstick within a casing; and a grip mesh within the casing with which the lipstick is in an integrated arrangement.

Although FIGS. 25A-1 through FIG. 31 are focused on lipsticks, other manufacturing processes that can be performed in accordance with the manufacturing processes disclosed herein may also be performed and be applied to non-lipstick products.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A suppository comprising:
   an active ingredient; and
   an inactive agent used to define a solid geometrical shape containing the active ingredient, the solid geometrical shape defining at least one gas flow path.

2. The suppository of claim 1, wherein the inactive agent is an inert agent.

3. The suppository of claim 1, wherein the gas flow path is arranged to communicate with a gas flow path of an element configured to be employed to insert the suppository into a body cavity.

4. The suppository of claim 1, wherein the suppository is manufactured in the presence of and in contact with an element configured to be employed to insert the suppository into a body cavity.

5. The suppository of claim 1, wherein the suppository is a solid or semi-solid suppository.

6. The suppository of claim 5, wherein the active ingredient is a pharmacological agent for treating a digestive disease.

7. The suppository of claim 6, wherein the digestive disease is ulcerative proctitis or distal colitis.

8. The suppository of claim 1, wherein the solid geometrical shape comprises a first open end and a second open end, the at least one gas flow path extending through the solid geometrical shape from the first open end to the second open end.

9. The suppository of claim 8, wherein the solid geometrical shape is rounded at the first open end and the second open end.

10. The suppository of claim 1, wherein solid geometrical shape is cylindrical.

11. The suppository of claim 1, wherein the solid geometrical shape is a hollow bullet shape comprising an open space defining the at least one gas flow path.

12. The suppository of claim 1, wherein the inactive agent is an oil-based fat or a polyethylene glycol.

13. The suppository of claim 5, wherein the active ingredient is a pharmacological agent for treating hemorrhoids.

* * * * *